(12) United States Patent
Blumenfeld et al.

(10) Patent No.: US 6,867,851 B2
(45) Date of Patent: Mar. 15, 2005

(54) SCANNING OF BIOLOGICAL SAMPLES

(75) Inventors: Martin Blumenfeld, Minneapolis, MN (US); Joseph J. Talghader, Eden Prairie, MN (US); Mark A. Sanders, Minneapolis, MN (US); Scott A. Nelson, Eagan, MN (US); Kraig Anderson, Woburn, MA (US); Steven A. Lewis, Bloomington, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 55 days.

(21) Appl. No.: 10/211,113

(22) Filed: Aug. 2, 2002

(65) Prior Publication Data

US 2003/0151735 A1 Aug. 14, 2003

Related U.S. Application Data

(63) Continuation-in-part of application No. 09/852,375, filed on May 10, 2001, which is a continuation-in-part of application No. 09/434,027, filed on Nov. 4, 1999, now Pat. No. 6,784,982.

(51) Int. Cl.[7] .............................................. G01N 21/03
(52) U.S. Cl. ....................................................... 356/73
(58) Field of Search .............................. 356/73, 36–50, 356/300–343; 250/458.1; 436/164–169, 805–811, 175–180; 422/102–106

(56) References Cited

U.S. PATENT DOCUMENTS

| 5,293,563 A | 3/1994 | Ohta |
| 5,378,883 A | 1/1995 | Batterman et al. |
| 5,459,325 A | 10/1995 | Hueton et al. |
| 5,552,322 A | 9/1996 | Nemoto et al. |

FOREIGN PATENT DOCUMENTS

| DE | 199 14 279 C1 | 9/2000 |
| EP | 0 973 040 A2 | 1/2000 |
| WO | WO 99/36578 | 7/1999 |
| WO | WO 00/12123 | 3/2000 |
| WO | WO 00/68670 | 11/2000 |

OTHER PUBLICATIONS

IMAGETEAM™ 4710HD/HD10—Fixed Mount 2D Image Reader Product Data Sheet (online). Hand Held Products, 1999–2001 (retrieved on Nov. 7, 2001), 2 pgs, http://www.handheld.com/HTMLDocs/4710HD–SS_Rev. B.pdf.

Beattie et al., "Hybridization of DNA Targets to Glass–Tethered Oligonucleotide Probes," *Mol. Biotechnol.*, 1995, 4:213–225.

(List continued on next page.)

*Primary Examiner*—Tu T. Nguyen
(74) *Attorney, Agent, or Firm*—Fish & Richardson P.C., P.A.

(57) ABSTRACT

An image detection apparatus comprises a light source and a holding apparatus adapted to hold a substrate on which a biological sample may be mounted. Light from the light source impinges on the biological sample and causes light that is representative of the sample to be emitted from the sample. A light detector is positioned in the path of the emitted light and is scanned across the emitted light. The emitted light may be focused on the light detector with an optical assembly. The emitted light may be generated by chromophores on probes in the biological sample.

45 Claims, 24 Drawing Sheets

U.S. PATENT DOCUMENTS

| | | |
|---|---|---|
| 5,552,928 A | 9/1996 | Furuhashi et al. |
| 5,556,529 A | 9/1996 | Nemoto |
| 5,556,539 A | 9/1996 | Mita et al. |
| 5,556,752 A | 9/1996 | Lockhart et al. |
| 5,578,832 A | 11/1996 | Trulson et al. |
| 5,593,839 A | 1/1997 | Hubbell et al. |
| 5,599,695 A | 2/1997 | Pease et al. |
| 5,631,734 A | 5/1997 | Stern et al. |
| 5,633,724 A | 5/1997 | King et al. |
| 5,672,881 A | 9/1997 | Striepeke et al. |
| 5,710,000 A | 1/1998 | Sapolsky et al. |
| 5,733,729 A | 3/1998 | Lipshutz et al. |
| 5,744,305 A | 4/1998 | Fodor et al. |
| 5,753,788 A | 5/1998 | Fodor et al. |
| 5,770,456 A | 6/1998 | Holmes |
| 5,770,722 A | 6/1998 | Lockhart et al. |
| 5,831,070 A | 11/1998 | Pease et al. |
| 5,834,758 A | 11/1998 | Trulson et al. |
| 5,837,832 A | 11/1998 | Chee et al. |
| 5,843,655 A | 12/1998 | McGall |
| 5,856,101 A | 1/1999 | Hubbell et al. |
| 5,856,104 A | 1/1999 | Chee et al. |
| 5,856,174 A | 1/1999 | Lipshutz et al. |
| 5,858,659 A | 1/1999 | Sapolsky et al. |
| 5,861,242 A | 1/1999 | Chee et al. |
| 5,871,628 A | 2/1999 | Dabiri et al. |
| 5,874,219 A | 2/1999 | Rava et al. |
| 5,885,837 A | 3/1999 | Winkler et al. |
| 5,889,165 A | 3/1999 | Fodor et al. |
| 5,919,523 A | 7/1999 | Sundberg et al. |
| 5,922,591 A | 7/1999 | Anderson et al. |
| 5,925,525 A | 7/1999 | Fodor et al. |
| 5,928,905 A | 7/1999 | Stemmer et al. |
| 5,945,334 A | 8/1999 | Besemer et al. |
| 5,959,098 A | 9/1999 | Goldberg et al. |
| 5,968,740 A | 10/1999 | Fodor et al. |
| 5,974,164 A | 10/1999 | Chee |
| 6,140,653 A * | 10/2000 | Che .................. 250/458.1 |
| 6,229,635 B1 | 5/2001 | Wulf |
| 6,448,088 B1 * | 9/2002 | Levine et al. ............ 436/164 |

OTHER PUBLICATIONS

Cohen et al., "Covalent attachment of DNA oligonucleotides to glass," *Nucleic Acids Res.*, 1997, 25(4):911–912.

Hoffman, "Biologically Functional Materials," *Biomaterials Science*, Ratner et al. (eds.), Academic Press, London, 1996, pp. 124–130.

Laursen and Machleidt, "Solid–Phase Methods in Protein Sequence Analysis," *Methods of Biochemical Analysis*, 1980, vol. 26, Glick (ed.), John Wiley & Sons, Inc., pp. 201–284.

May and Heebner, "Laboratory Technology Trends—The Power of Proteomics," *Science*, 2001, 292:317–318, 322, 326, 328, 335, 337, 340, 342, 344.

Millard, "Preparation of Glass Plates with Cerium Oxide for DNA Sequencing," *Bio Techniques*, 1995, 19(4):576.

Rogers et al., "Immobilization of Oligonucleotides onto a Glass Support via Disulfide Bonds: A Method for Preparation of DNA Microarrays," *Anal. Biochem*, 1999, 266:23–30.

* cited by examiner

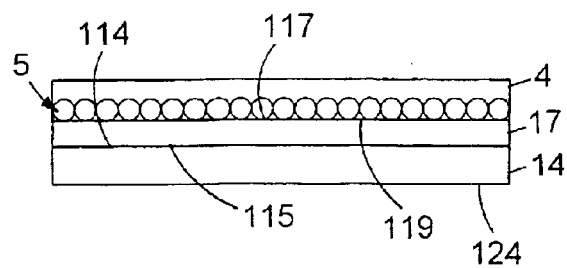
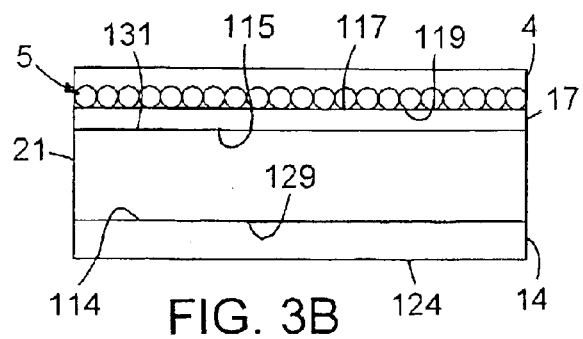
FIG. 3A    FIG. 3B
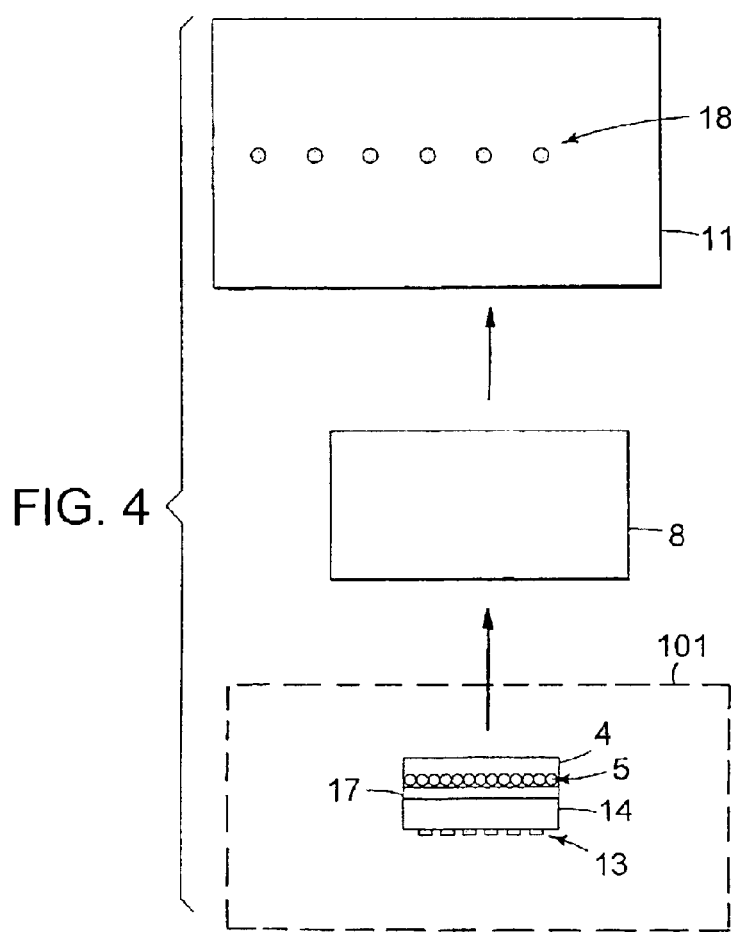
FIG. 4

SCANNING OF BIOLOGICAL SAMPLES

CROSS-REFERENCE TO RELATED APPLICATIONS

This application is a continuation-in-part of U.S. patent application Ser. No. 09/852,375, filed on May 10, 2001, which is a continuation-in-part of U.S. patent application Ser. No. 09/434,027, filed on Nov. 4, 1999, now U.S. Pat. No. 6,784,982 both of which are incorporated herein by reference.

FIELD OF THE INVENTION

The present invention pertains to imaging systems and methods. More particularly, the present invention relates to imaging and/or mapping of biological samples using electronic light detectors.

BACKGROUND OF THE INVENTION

Various conventional approaches have been used to visualize the surface of a biological sample, e.g., DNA spots of a micro-array such as a DNA chip, protein bands in a one dimensional (1-D) or two dimensional (2-D) gel, etc. For example, a DNA chip is generally a rigid flat surface, typically glass or silicon, that may have short chains of related nucleic acids spotted, e.g., DNA spots, in rows and columns, i.e., an array, thereon. Hybridization between a fluorescently-labeled DNA and specific locations on the chip can be detected and analyzed by computer-based instrumentation. The information derived from the results of hybridization to DNA chips is stimulating advances in drug development, gene discovery, gene therapy, gene expression, genetic counseling, and plant biotechnology.

Hybridization to DNA chips can be monitored by fluorescence optics, by radioisotope detection, and by mass spectrometry. The most widely-used method for detection of hybridization employs fluorescently-labeled DNA, and a computerized system featuring a confocal fluorescence microscope (or an epifluorescence microscope), a movable microscope stage, and DNA detection software. Technical characteristics of these microscope systems are described in U.S. Pat. Nos. 5,293,563; 5,459,325; and 5,552,928, which are all incorporated herein by reference. Further descriptions of imaging fluorescently immobilized biomolecules and analysis of the images are set forth in U.S. Pat. Nos. 5,874,219; 5,871,628; 5,834,758; 5,631,734; 5,578,832; 5,552,322; and 5,556,529, which are all incorporated herein by reference.

In brief, these conventional approaches to visualizing the surface of a DNA chip involve placing the chip on a stage of a microscope, moving the stage to put the sample into focus with a microscope objective, and triggering a digital camera or similar device to capture an image. The microscope objective is generally a device made of a group of lenses that have a sophisticated design that collects light from the sample, magnifies the image of the sample, and minimizes the unavoidable image and color distortion caused by the passage of the light through the objective. The light collected from the sample may pass through the microscope objective and through a set of mirrors and lenses until it is delivered to an eyepiece or the camera. The light path is the path that the light takes from the point where it leaves the surface of the sample until it reaches an imaging device such as an eyepiece or camera. The microscope generally is associated with a light source that directs light onto the sample.

These microscopes also generally have sets of optical filters that allow for viewing of fluorescent images. For example, the DNA that is hybridized to the surface of the DNA chip is typically labeled with fluorescent molecules that absorb light at one wavelength and then emit a different wavelength. The microscope may be equipped with sets of optical filters that block the wavelengths of light from the light source associated with the microscope but which allow the light emitted by the fluorescent molecules to pass therethrough such that the light may reach the eyepiece or camera. The light source is typically integral with the microscope and is an important part of the imaging system.

Further, generally, 1-D and 2-D electrophoresis processes are electrophoretic methods for resolving complex mixtures of proteins, e.g., 2-D electrophoresis is a multiple step process for resolving complex mixtures of proteins. For example, in 2-D electrophoresis, the proteins in a sample may first be dissociated into polypeptide subunits by dissolving in an appropriate buffer. The sample may then be applied to the top of a tube gel containing ampholines. Isoelectric focusing (IEF) is then carried out in the first dimension. After the IEF is carried out, the gel which contains the peptides is removed from the gel tube and placed over a slab gel and sealed by overlapping stacking gel; and thereafter, the second dimension of slab gel electrophoresis is carried out (e.g., proteins (negatively charged) run from the top of the slab (held at a negative charge) toward the bottom of the slab (held at a positive charge)). Then, staining, e.g., using a stain that binds to proteins so they can be identified, and an optional drying step, is carried out. Thus, the polypeptides are separated according to the independent parameters of isoelectric point in the first dimension and molecular weight in the second dimension (e.g., protein bands). For example, a large number, e.g., 1000, polypeptide spots (e.g., protein bands) may be resolved on a single two dimensional gel. Further, for example, such proteins in a 2-D gel may be labeled with fluorescent or chemi-luminescent markers.

Such protein bands in 1-D and 2-D electrophoresis may also be visualized and analyzed. Like DNA chips, such visualization of the protein bands in the 2-D gel is generally performed using the same conventional approaches as used to visualize the surface of a DNA chip, e.g., a microscope with the sample put into focus using a microscope objective, a digital camera, etc.

These conventional microscopes are sophisticated and expensive instruments that require training and maintenance. A single microscope objective typically has multiple lenses that are generally very expensive. A lens generally refers to a transparent solid material shaped to magnify, reduce, or redirect light rays, e.g., focus light. A light filter or mirror is distinct from a lens. Furthermore, use of a microscope requires a dedicated workspace that is approximately the size of a typical desk. Conventional microscopes have a light path that is several centimeters long that transmits collected light through air and other assorted optical devices within the light path. One of the challenges in microscopy is making the microscope as efficient as possible in capturing all of the light that leaves the sample surface so that an optimal image can be captured.

This costly instrumentation conventionally used to image biological samples, e.g., DNA chips, impedes the broad usage of such technologies. Therefore, an inexpensive, low-maintenance alternative spot detection method and apparatus for biological sample analysis, e.g., DNA chip analysis, that is easy to use and requires a minimum of space and maintenance is needed.

Integrated electronic circuit arrays for light-detection (e.g., a member of a group of detectors referred to as electronic light detectors) are readily available. They generally are based on CCD (charge-coupled device) or CMOS (complementary metal oxide semiconductor) technologies. Both CCD and CMOS image detectors are generally two-dimensional arrays of electronic light sensors, although linear imaging detectors (e.g., linear CCD detectors) that include a single line of detector pixels or light sensors, such as, for example, those used for scanning images, are also available. Each array includes a set of known, unique positions that may be referred to as having addresses. Each address in a CCD or CMOS detector is occupied by a sensor that covers an area (e.g., an area typically shaped as a box or a rectangle). This area occupied by a single sensor is generally referred to as a pixel or pixel area. As used herein, a light-detecting sensor located in a pixel area is referred to as a detector pixel. A detector pixel, as generally used herein, may be a CCD sensor, a CMOS sensor, or any other device or sensor that detects or measures light. The sizes of detector pixels vary widely and may have a diameter or length of 0.2 μm, which is also the theoretical limit of resolution of a light microscope. It is noted that some detectors have resolving sizes lower than 0.2 μm, such as for use in microscopes employing light of wavelengths of 180 nm and below.

CCD detectors, widely used in consumer and scientific applications such as digital recorders and digital cameras, are sensitive, and may be made with detector pixels that are smaller than those of CMOS devices. CMOS devices are now beginning to be incorporated in recorders and cameras because they are less expensive to produce. CMOS devices also are easier to interface with external control systems than CCD detectors. Some readily-available CMOS devices are integrated with the capabilities to provide acquiring, digitizing, and transmitting an image without additional circuitry, while CCD detectors generally require additional circuit elements to accomplish the same tasks.

SUMMARY OF THE INVENTION

A system and method are provided for detecting an image representative of a biological sample. In the system, a light detector acquires light that is emitted from the biological sample. The detector does not at once detect all of the light that can be emitted by the biological sample. Instead, the detector is scanned across the sample and detects multiple images that together make up an image of the sample. For example, the detector may be a linear CCD and may gather "slices" of the sample that may later be combined into a full image. The detector may be scanned across the sample by holding the sample steady while moving the detector through light emitted from the sample.

In one embodiment, an apparatus has a light source that generates source light along a source light path, a holding apparatus, and a linear light detector. The holding apparatus can hold a substrate on which a biological sample is mounted in a position such that at least a portion of the source light impinges on at least a portion of the biological sample, and causes fluorescence representative of the biological sample to be produced in the form of emitted light along an emitted light path. A linear light detector array comprising a plurality of detector pixels is positioned in at least a portion of the emitted light path and senses emitted light from the biological sample. And, a transport mechanism translates the light detector array to capture an image of at least a portion of the sample as a plurality of sub-images.

In another embodiment, an image detection system is provided having a light source that provides source light along a source light path, a holding apparatus, and a light detector. The holding apparatus holds a biological sample in at least a portion of the source light path so that source light impinges on at least a portion of the sample, thereby producing emitted light that is representative of the biological sample along an emitted light path. A light detector is mounted in at least a portion of the emitted light path and can be moved relative to the emitted light path so as to scan across an image representation of the biological sample. The system may have a fixed focus apparatus, and may have a depth of field of greater than approximately 50 microns.

A method for detecting an image is also provided, in which a biological sample is provided in a sampling position. Source light impinges on the sample such that, in response to the impinging light, light representative of the sample is produced along an emitted light path. A light detector array is positioned in proximity to the biological sample and intersecting the emitted light path. The array is scanned across a portion of the light representative of the biological sample. The array may be a linear array and may take the form of a charge coupled device.

In one embodiment, the light source may be comprised of a plurality of diodes. More particularly, the light source may be comprised of a first set of light emitting diodes or laser diodes that generate light in a first wavelength range and a second set of diodes that generate light in a second wavelength range that is substantially different than the first wavelength range. A filter may be used to reduce interference between the source light and the emitted light.

The light emitted from the biological sample may include light generated by the sample itself, including light of chemi-luminescence, fluorescence, chemi-fluorescence, photon excitation, phosphorescence, adsorption and quenching thereof. For example, the biological sample may be in the form of a micro-array comprising one or more sequences of nucleic acids immobilized to a substrate at a particular micro-array address. The nucleic acid sequences may be positioned such that emitted light from a micro-array address is substantially directed onto at least one detector pixel of the light detector array. The light from a single address may also be directed to a single detector pixel. The substrate may be opaque, and the light path of the emitted light may not pass through any part of the substrate.

The light detector array may be movable relative to the emitted light path by translating the light detector array. Moreover, a lens assembly may be positioned in the emitted light path to focus the light on the light detector. In addition, a chip transport mechanism, such as a rotary mechanism, may be provided with, or in addition to, the system so that multiple samples may be imaged without intervention from an operator.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 3A and 3B illustrate two alternative arrangements of optical components for direct mapping in an electronic light detector array detection system according to the present invention;

FIG. 4 is a block diagram of an alternate embodiment of an electronic light detector array detection system according to the present invention;

Like reference symbols in the various drawings indicate like elements.

DETAILED DESCRIPTION OF THE EMBODIMENTS

Figure 1:
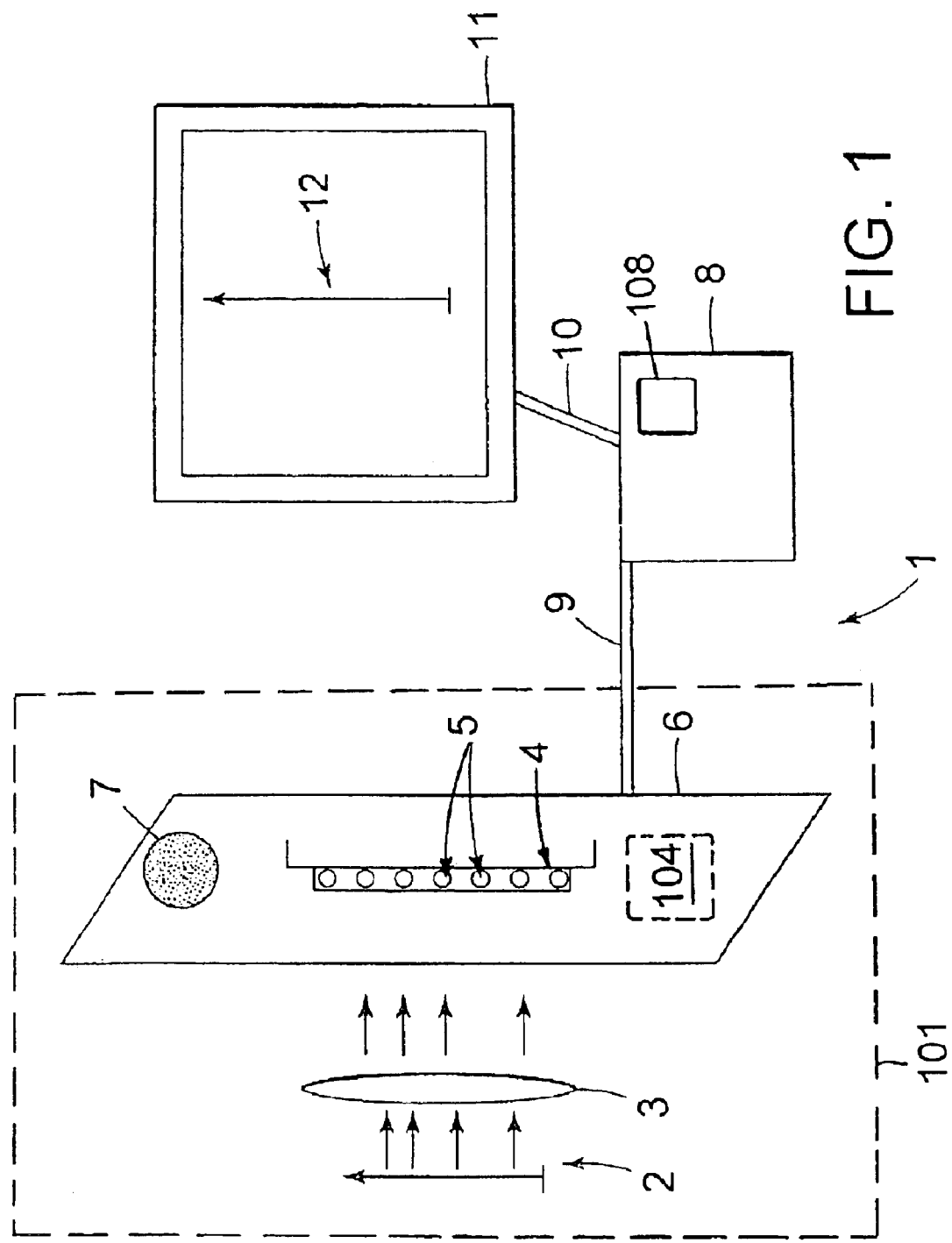
FIG. 1 illustrates the components and general function of an electronic light detector array system according to the present invention for imaging a biological sample.

The present invention provides inexpensive devices and methods for resolving light (e.g., emitted light by fluorescent labeled nucleic acid spots) representative of biological samples (e.g., nucleic acid spots on a micro-array such as a DNA chip, protein bands of a 1-D or 2-D gel, etc.) for the detection thereof. As used herein, biological samples refers to biological material (proteins, nucleic acids, tissues, etc.) associated with a biological material holding structure (e.g., a micro-array substrate such as a DNA chip substrate, a gel, etc.) in a manner that allows for detection of the biological material, or portions thereof (e.g., with the use of markers such as dyes, tags, labels, or stains), such as through the use of imaging (e.g., direct mapping).

The term, "biological samples" refers not only to the biological material itself (proteins, nucleic acids, tissues, etc.) but also to other materials associated therewith used for detection of the biological material, or portions thereof (e.g., dyes, labels, stains, or any other marker used in the identification of materials). As used herein, biological material refers to, for example, a sample of tissue or fluid isolated from a subject, including but not limited to, for example, blood, plasma, serum, fecal matter, urine, bone marrow, bile, spinal fluid, lymph tissue and lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. A biological sample can include, for instance, a polypeptide or a polynucleotide, or could also include intact or fragmented portions of organisms or cells obtained from sampling the environment, such as airborne pathogens.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like.

Also, as used herein, the term "polynucleotide" refers to a polymeric form of nucleotides of any length, either ribo-nucleotides or deoxynucleotides, and includes both double- and single-stranded DNA and RNA. A polynucleotide may include nucleotide sequences having different functions, including for instance coding sequences, and non-coding sequences such as regulatory sequences. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

One or more embodiments of the present invention are operable for use in multiple imaging applications, e.g., imaging of two-dimensional and three-dimensional objects, such as fluorescence imaging, reflective imaging, bar code imaging, densitometry, gel documentation, or in any other application wherein imaging of a biological sample is beneficial. One or more of the systems and methods as described herein may be used for ultra-sensitive sample detection. One or more of the imaging systems and methods of the present invention are flexible (e.g., can image various objects and perform various types of imaging such as fluorescence and reflective imaging) light imaging systems with the ability to produce high-quality images from, for example, various biological sample configurations that use, for example, single color fluorescence, multiple color fluorescence, chemi-luminescence, chemi-fluorescence, colorimetric detection, densitometry, or any other technique detectable through imaging. Such image quality, e.g., spatial resolution, is dependant, at least in part, on the lens and electronic light detector used in such systems. Such imaging provides the ability for filmless detection. At least some of the imaging systems and methods of the present invention provide for the rapid production of single-color and multi-color fluorescence images, e.g., images showing fluorescent positions such as regions, spots, areas, etc., of a biological sample (e.g., fluorescent positions on a micro-array or DNA chip) when such material is caused to fluoresce by a light source. A wide range of samples, including, but not limited to gels, blots, micro-arrays, micro-plates, etc. may be imaged to detect fluorescent positions. Such methods and systems have a high sensitivity for detection of fluorescent dyes and labels, including, but clearly not limited to, ethidium bromide, SYBR® Green, SYBR® Gold, SYPRO®, Radiant Red, fluorescein (FITC), rhodamine, Cy2, Cy3, Texas Red, Green Fluorescent Protein (GFP).

With regard to chemi-luminescence imaging, light emitted by biological samples is detected using one or more imaging systems and methods of the present invention. For example, horse radish peroxidase (HRP) and alkaline phosphatase (AP) activated biological samples may be detected with suitable quality and accurate quantitation. Further, for example, high sensitivity detection of, for example, proteins, using enhanced chemi-luminescence (ECL), e.g., detection of western dot blots and chemi-fluorescent substrates such as AttoPhos and ECL-Plus, may be attained. Further, with respect to densitometry and colorimetric imaging, various colorimetric stains, including, but clearly not limited to, Coomassie Blue, copper, zinc, and silver stain may be detected.

Portions of the following description is primarily provided, for simplicity, with reference to use of microarrays such as DNA chips. However, one skilled in the art will recognize that the present invention is applicable to any imageable biological sample, e.g., 1-D gels, 2-D gels, blots, substrates having biological material thereon. For example, as previously noted, such systems and/or methods may be used to image two-dimensional gels, e.g., fluorescent labeled protein bands of such gels. Thus, polypeptides separated according to the independent parameters of isoelectric point and molecular weight (e.g., protein bands) can be imaged using the present invention.

The smallest diameter DNA spot generally attainable on a micro-array, e.g., a DNA chip, approximates the diameter or length of a detector pixel, e.g., about 10 µm, of a conventional electronic light detector array, e.g., CMOS light detector array. Therefore, if the DNA array on the DNA chip and the detector pixels of the electronic light detector, e.g., CMOS light detector array, are in close proximity to each other, the light emitted by each spot of a DNA array can be directly mapped to a limited number of detector pixels in the electronic light detector array. Such direct mapping would eliminate the expensive optical systems that are conventionally required for DNA chip analysis, and, by lowering the cost, expand the potential applications of DNA chip technology.

For example, one embodiment of a system and/or method according to the present invention may include direct mapping of light emitted by a single DNA spot onto one or more corresponding detector pixels of an electronic light detector array. Further, for example, one embodiment of a system and/or method may position the DNA chip in direct physical contact with an electronic light detector array. In a modification of such systems or methods, a simple optical system, such as a single mapping lens, may be used to map an enlarged or reduced version of the DNA spot array onto an electronic light detector array. Further, for example, a modified bar code reader may be used to image a biological sample for detection of biological material thereof, or portions of such biological material. As described further below, computer software is used to process the data from the electronic light detector array system. For example, the data may be treated as a two-dimensional map, or otherwise processed as an array of data.

An imaging system according to the present invention may be used to replace expensive optical detection systems currently employed for DNA chip analysis. In general, one embodiment of such a system may include an electronic light detector array, a filter, and, optionally, a mapping lens apparatus that enables a DNA chip having an array of DNA spots to be mapped onto the electronic light detector array. For example, each position on the DNA chip surface has a corresponding position or set of positions, i.e., detector pixels, on the electronic light detector array. Light associated with the array of DNA spots, e.g., fluorescence, at an address on the DNA chip surface is received or sensed at one or more known addressed detector pixels or set of detector pixels.

Such imaging, e.g, mapping of biological sample information to detector pixels, is inexpensive. It eliminates the need for a complicated microscope that requires maintenance and trained personnel. It may capture light directly from a DNA sample. By eliminating many lenses, the disadvantages stemming from use of many lenses are reduced. Further, such mapping may enable direct capture of light so that a maximal amount of light is captured from the sample. Such minimization of the loss of light creates a sensitive imaging system.

Electronic light detector direct mapping may be considered analogous to the established photographic method known as contact printing. In contact printing, a photographic negative is placed in direct contact with unexposed photographic paper, and illuminated briefly. When the photographic paper is subsequently developed, its image has a 1:1 correspondence to the negative.

FIG. 1 generally illustrates components of and the general function of an electronic light detector array detection system 1, e.g., a CMOS-based detector array system, which is used to acquire a visual image 2 of a biological sample that includes biological material associated with a biological material holding structure (e.g., a DNA spot array on a DNA chip, protein bands in a 2-D gel, etc.), reconstruct the image, and display a reconstructed visual image 12. Such image data may then be analyzed as desired, either manually or by appropriate software operable upon such image data.

For example, when examining and analyzing DNA arrays on chips, similarities and/or differences between portions of the array and/or similarities and/or differences between arrays of multiple chips may be noted. In other words, for example, using the images provided herein, a user, e.g., a human or a machine, may note certain biological material or spots that are alike when they are conditioned in the same way, or pick out spots that are different than the majority of the other spots of the array. Further, for example, the user may compare two or more arrays to see if they are similar or the same, e.g., 90% the same, identical, etc. Similar examination and analysis may occur for other types of biological samples.

The electronic light detector array detection system 1 includes an image detection apparatus 101 that senses light representative of the visual image 2 using detector pixels, e.g., CMOS detector pixels 5, of an electronic light detector 4, e.g., a CMOS detector array. The image detection apparatus 101 provides electrical signals generated upon detection of such light representative of image data in a useable form to a computer 8 of the system 1, such as via a communications cable 9.

An electronic light detector, as used herein, may be any suitable electronic circuit array operable for light-detection. Generally, such detectors 4 are based on CCD (charge-coupled device) or CMOS (complementary metal oxide semiconductor) technologies. Both CCD and CMOS image detectors are generally two-dimensional arrays of electronic light sensors, although linear imaging detectors (e.g., linear CCD detectors) that include a single line of detector pixels or light sensors, such as, for example, those used for scanning images, may also be suitable depending on the embodiment described herein. Each array includes a set of known, unique positions that may be referred to as having addresses. Each address in a CCD or CMOS detector is occupied by a sensor that covers an area (e.g., an area typically shaped as a box or a rectangle). This area occupied by a single sensor is generally referred to as a pixel or pixel area. As used herein, a light-detecting sensor located in a pixel area is referred to as a detector pixel. A detector pixel, as previously described herein, may be a CCD sensor, a CMOS sensor, or any other device or sensor that detects or measures light. The sizes of detector pixels vary widely and may have a diameter or length of 0.2 $\mu$m, which is the theoretical limit of resolution of a light microscope. Light, as used herein, refers to any electromagnetic emission of at least 120 nm wavelength and includes ultraviolet, visible, and infrared light.

Various other associated equipment or components may be found in association with electronic light detectors, and are known to those skilled in the art. For example, such equipment may include manual or electric filter-switchers, movable mirrors, and motors and controls to raster a laser across a sample. Further, for example, various equipment or components are associated with CCD and CMOS sensors, which are incorporated into a myriad of commercially available cameras and detectors. For instance, various equipment and techniques are known for producing a color image using red, green, and blue (e.g., magenta, green, and cyan) detection. For example, an image may be split into three images, each of which is sent through a red, green, or blue filter to a CCD sensor or CCD sensors. A sample may be placed on a chip with different sensitivities to red, green, and blue light. Such equipment and components include techniques (e.g., software processes or algorithms) and electronic circuitry for improving an image, and may include, for example, electronic filters (high-pass, low-pass, etc.), time and frame-averaging, image subtraction, and other techniques known to those skilled in the art.

In the computer 8, the image data is stored, e.g., addressed or mapped, in, for example, the computer's video memory 108. The image data may be processed to provide data representative of a reconstructed image 12 which may be provided, e.g., passed by a cable 10, for display on a monitor 11, e.g., a computer display or any other display apparatus that may display image data representative of the reconstructed image 12.

As shown in FIG. 1, in one illustrative embodiment of the image detection apparatus 101, light representative of the visual image 2 is collected by a mapping lens 3 of the illustrative image detection apparatus 101, which focuses the light representative of the visual image 2 onto detector pixels 5, e.g., CMOS detector pixels or CCD detector pixels, of a detector 4, e.g., a CMOS detector array, a CCD array, or any other light detecting device having detector pixels to which light from the biological sample can be mapped. The light may be any type of light representative of the biological sample, e.g., luminescence from the sample, fluorescence from the sample, etc. The electronic light detector array or detector 4 contains a plurality of detector pixels 5. The detector array or detector 4 is positioned and/or mounted on a substrate or circuit board 6, which is associated with and/or contains a power supply 7, e.g., a direct current power supply, for the detector 4.

The detector array or detector 4 may have electronic circuitry 104 associated therewith or may include electronic circuitry, e.g. analog to digital conversion circuitry, buffer circuitry, amplification circuitry, etc., that converts electrical signals generated upon detection of light by the detector pixels 5 to useable form by computer 8, e.g., digital form. Such electronic circuitry, e.g., circuitry 104, may be used to facilitate the transfer of the digitized signal representative of the sensed light to the computer 8 via the communications cable 9. In the computer 8, the digital signal is stored as image data, e.g., addressed or mapped, to the computer's video memory 108. The image data is processed to provide data representative of a reconstructed image 12 which may be provided, e.g., passed by the cable 10, for display on monitor 11, e.g., a computer display or any other display apparatus that may display image data representative of the reconstructed image 12.

The electronic light detector 4 may be used in various configurations to image biological samples for the detection of biological material, or portions thereof, associated with holding structure of the biological sample (e.g., holding structure such as gels, DNA chip substrates, micro-titer plates, etc.). Generally, such configurations fall into two broad categories: transmissive imaging and reflective imaging.

As used herein, transmissive imaging configurations refer to configurations that provide for detection of light from a biological sample, e.g., from the sample surface at which biological material is associated, which requires the use of transmitted light through all, or at least a major portion of, the biological holding structure, e.g., DNA chip substrate, micro-titer plates, gels that may be associated with a substrate or imaged alone, etc. For example, the transmitted light may be an excitation light that travels through the biological material holding structure to excite biological material (e.g., tags thereof) which then emits light that travels in a light path (which as defined herein refers to the path light travels from the point where it leaves the biological sample until it reaches the electronic light detector) and impinges on one or more detector pixels. Alternatively, the transmitted light may be fluorescence emitted by biological material (e.g., biological material excited by an excitation light source) that travels through the biological holding structure (e.g., the biological material holding structure is part of the light path) prior to impinging on the one or more detector pixels.

In other words, for the electronic light detector 4 to detect light from the biological sample, light (whether excitation or fluorescence) is passed through the biological material holding structure of the biological sample. In such cases, the biological material holding structure must be light transparent structure, e.g., glass, clear materials, or other materials that permit transmission of suitable or desirable wavelengths of light. For example, such configurations are shown in FIGS. 2–5 and 8–11.

On the other hand, as used herein, reflective imaging configurations generally, although not always, refer to configurations that provide for detection of light from a biological sample, e.g., a sample surface at which biological material is associated, which does not require the use of transmitted light through the biological material holding structure, or a major portion thereof, e.g., DNA chip substrate, micro-titer plates, gels that may be associated with a substrate or imaged alone, etc. For example, light reflected from a biological sample may travel in a light path that does not include the biological material holding structure. However, such configurations can be used when light is transmitted through all or a part of the biological material holding structure. For example, such configurations may provide for detection of light from a sample surface at which biological material is associated which requires the use of transmitted light through all, or at least a major portion of, the biological holding structure.

In other words, for the electronic light detector 4 to detect light in a reflective imaging configuration from the biological sample, light (whether excitation or fluorescence) may or need not pass through the biological holding structure of the biological sample. Preferably, light does not pass through the biological material holding structure or at least does not pass through a major portion thereof. As used herein, a major portion refers to a portion greater than 50 percent, e.g., 50 percent of the thickness of the substrate. In such cases, the biological holding structure need not be light transparent structure, but rather can be opaque materials, e.g., nitrocellulose, charged nylon, silicon as a substrate for micro-array formation, etc., which have more favorable properties than light transparent structure (e.g., glass). Such reflective imaging configurations are shown in FIGS. 6–7 and 12–14, where, for example, excitation light excites fluorescent markers of biological material and is reflected from a sample surface along with fluorescence being provided via a light path from the biological sample to the electronic light detector, or, further, for example, where illumination light is reflected from the biological sample via a light path to detector pixels representative of at least absorption characteristics of the biological sample.

In many cases, but clearly not in all cases, in the transmissive imaging configurations involving DNA chips, the detector pixels of the electronic light detector are facing an opposing side of a biological material holding structure, e.g., DNA chip substrate. The opposing side is a side opposite of the sample surface upon which biological material is provided. However, the opposing side and the detector pixels are not necessarily directly in contact or directly facing each other as they may be separated by filters, lenses, etc.

Preferably, in many cases, according to the present invention, the detector pixels of the electronic light detector in a reflective imaging configuration (e.g., involving DNA chips) are facing the sample surface upon which biological material is provided. However, the sample surface and the detector pixels are not necessarily directly in contact with one another or directly facing one another as filters, and lenses may be located therebetween.

As used herein, surfaces and/or portions of components that are facing one another are not necessarily directly facing each other, e.g., other elements such as filters, lenses, etc. may separate such surfaces and/or portions of components. Further, as used herein, directly facing refers to surfaces and/or portions of components that are immediately next to one another but not necessarily in direct contact. Further, preferably, although not necessarily, facing surfaces and/or portions of components (e.g., detector pixels arrays) are parallel to one another.

Figure 2:
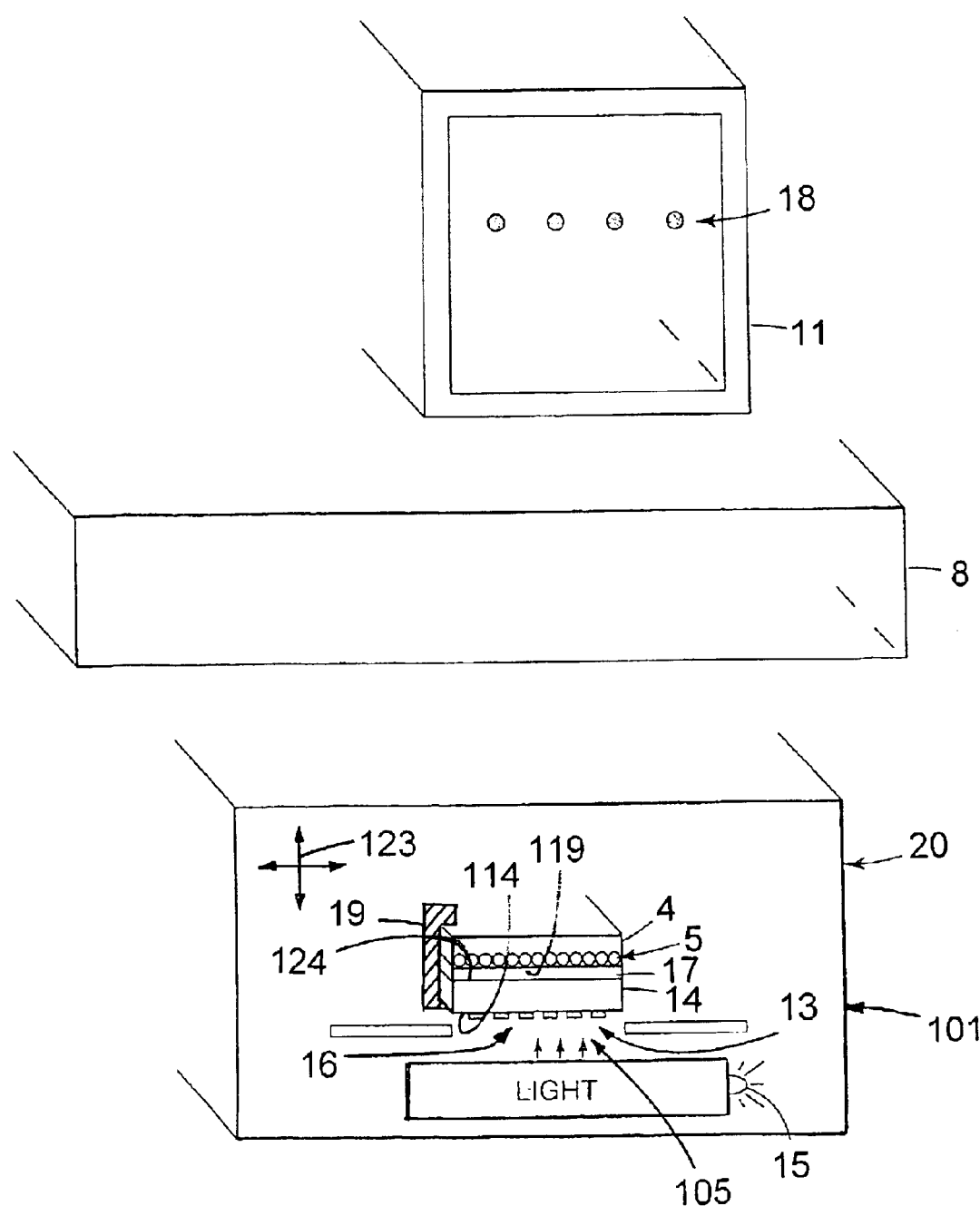
FIG. 2 illustrates the use of direct mapping to acquire and reconstruct light representative of DNA spots of a DNA chip in an electronic light detector array detection system such as that shown in FIG. 1.

FIG. 2 illustrates an exemplary embodiment of an image detection apparatus 101 used in a system to acquire and display an image 13 representative of sensed light associated with a biological sample 14, e.g., light emitted by a DNA chip 14 that is excited with ultraviolet or blue light 105 provided by a light source 15. A clamping system 19 holds the DNA chip 14, the electronic light detector array 4, and an optical filter 17 in contact with each other and in a sampling position.

In one embodiment of the image detection apparatus 101, the DNA chip 14 is loaded into the holding structure, e.g., clamping system 19 or any other type of holder, and the holder is then moved from a loading position into the sampling position. For example, a sliding mechanism may be used to slide the holder from the loading position into the sampling position. Further, any other electrical and mechanical structure may be used to perform such movement features, e.g., a motor may be used to move the DNA chip 14. For example, with the DNA chip loaded into the holder in a loading position, a switch may be activated to turn a motor on so as to slide the holder to the sampling position. It will be recognized that such loading and positioning structure and methods may be used for any of the embodiments described herein.

Further, it will be recognized that to focus the image, the holder may be moved to multiple sampling positions until a sampling distance desired by a user is achieved, e.g., an image is focused. For example, the electronic light detector along with any detection software or imaging software may be used along with, for example, a graphic display, to visualize the sample surface and the holder or part of the imaging apparatus may be moved to focus the image. Alternatively, the focusing may be automatically performed with use of a programmable computer. Movement of one or more components of the detection system is illustratively shown in FIG. 2 by arrows 123.

In this particular embodiment of FIG. 2, the DNA chip 14, the electronic light detector array 4, and the optical filter 17 are in direct contact with one another. In other words, one side 124 of the DNA chip 14 is in direct contact with, i.e., touching, one side of the optical filter 17, and further, the other opposing side of the optical filter 17 is in direct contact with one side of the detector 4 that includes detector pixels 5 for sensing light that impinges thereon.

However, one skilled in the art will recognize that although direct contact is preferred in some embodiments, in various other embodiments described herein, the components need not be in direct contact with one another. For example, the present invention may function suitably with the components in close proximity to one another at a distance that is suitable to accomplish mapping of pertinent information from the biological sample to a suitable number of detector pixels, e.g., a DNA spot to a few detector pixels. Generally, a distance of less than 100 $\mu$m is a distance less than, and which may provide beneficial advantages over, other microscopic detection systems that employ objective lens type optical systems.

Preferably, the sampling distance (or the traveling distance for light emanating from one or more portions of the sample to reach the detector pixels 5, i.e., the light path) for use in detection of spots of polynucleic acid or other biological material is of a shorter distance, e.g., a shorter light path, than used in such microscopic detection systems employing objective lens type systems as such shorter light paths provide for improved capture of light. Preferably, the light path in one or more embodiments herein is less than one centimeter; more preferably, the light path is less than four millimeters; even more preferably, the light path is less than one millimeter; more preferably, the light path is less than 200 microns; yet more preferably, the light path is less than 75 microns; yet even more preferably, the light path is less than 35 microns; and most preferably, the light path is less than 15 microns. Yet further, preferably, the light from the sample surface travels a substantially linear light path to the detector pixels 5.

In at least one embodiment, every point of the light path between where light leaves the biological sample and the detector pixels 5 has an index of refraction that is greater than 1.0. Further, in at least one embodiment, the light path is formed of solid materials, e.g., light travels through components that are in direct contact.

A light-tight enclosure 20 is provided to house components of the image detection apparatus 101 as shown in FIG. 2. The light 105 is directed through an aperture 16 and impinges on the DNA chip 14. In this particular embodiment, light 105 causes the emission of light from one more regions or portions of the DNA chip 14 that is excited by the ultraviolet or blue light 105. This emitted light from the excited regions of the DNA chip 14 passes through the chip substrate and an optical filter 17. The excitation light, e.g., the ultraviolet and/or blue light, is removed by the optical filter 17. The emitted light is then allowed to impinge on the detector pixels 5 of the electronic light detector array 4, e.g., a CMOS detector. For example, a CMOS detector 4 may contain circuitry that converts sensed analog light impulses to digital form, which can then be transmitted to computer 8, and ultimately after processing be displayed as reconstructed image 18 on a monitor 11.

An optical filter, as used herein, refers to a light filter that blocks or redirects the passage of some wavelengths of light and allows or redirects the passage of other wavelengths of light depending upon the application in which it is used, e.g., selective passage or redirection. Any suitable optical filter capable of performing such filter functions for a particular application may be used according to the present invention. Such optical filters include, for example, edge filters, narrow band filters, dichroic mirrors, and optical filters such as those used in the visualization arts, including optical, ultraviolet, confocal, and two- or multi-photon microscopy.

The light sources as used herein may include, for example, those commonly used in the visualization arts, including optical, ultraviolet, confocal, and two-photon or multi-photon microscopy. Further, for example, such light sources may include light lamps, LED cluster arrays, tungsten filaments, and light lasers, such as visible-light lamps, ultraviolet lamps, mercury lamps, and lasers, including argon lasers, helium-cadmium lasers, semiconductor lasers, LED lasers, etc.

With reference to the embodiment of the present invention shown in FIG. 2, an image detection apparatus 101 and method for detecting a pattern of, for example, polynucleic acid hybridization to a biological sample surface 114, e.g., a surface of a DNA chip 14, is further described. For example, the image detection apparatus 101 may include a positioning device, e.g., the clamping structure 19, for receiving a nucleic acid chip 14 and maintaining the chip 14 in a sampling position. The nucleic acid chip 14 is generally an object with a flat sample surface 114 and an opposed surface 124 that is joined to the sample surface 114 by a thickness. The sample surface 114 has sequences of nucleic acids immobilized thereto, with each sequence being immobilized to a particular chip address. Further, the electronic light detector array 4 includes the detector pixels 5 on side 119 of the electronic light detector 4. The detector pixels 5 include sensors located at particular detector pixel addresses. The sampling position places the sample surface 114 of the chip 14 at a defined position relative to the electronic light detector array 4 such that light leaving a chip address on the chip 14 is substantially directed through the light path that includes the biological material holding structure, e.g., DNA chip substrate, onto at least one detector pixel 5 with an address that is correlated to the chip address. In such a manner, the nucleic acid spots on the chip 14 are mapped to the detector pixels 5.

In one embodiment, a detection system according to the present invention, such as, for example, the system shown in FIG. 2, may be configured to excite, detect, filter, and process fluorescence from conventional fluorophores, for example, fluorophores described in catalogues published by Life Technologies, Inc. (Rockville, Md.), Sigma-Aldrich, Inc. (SIGMA, ALDRICH, and FLUKA brand names; St. Louis, Mo.), Pierce Chemicals (Rockford, Ill.), and other suppliers known to those skilled in the art. Similarly, other DNA visualization techniques are currently known and used, and many examples of these technologies are set forth in these same sources. For instance, colorimetric systems that create a color in the visible light wavelength, for instance those based on a stain or on enzyme activity, may be adapted to visualize DNA. Amplification systems that may be used in combination with a colorimetric or fluorescent system may also be used; for example, avidin-biotin or antibody-based techniques. For example, the target DNA labeled with biotin may be placed on the DNA chip. After a washing protocol is performed, the sample may be exposed to labeled avidin, which makes a strong bond to the biotin. The label on the avidin may be a fluorophore (or an enzyme such as horseradish peroxidase (HRP) that is suitable for calorimetric assay). Additionally, DNA may be marked or labeled using chemi-luminescence or chemi-fluorescence and subsequently detected.

DNA may be attached to biological material holding structures such as substrates, e.g., forming DNA chips, that pass light (e.g., light transparent DNA chips) in a variety of manners known to those skilled in the art. For example, glass or quartz may be treated with silanes to create carboxyl or amine groups that may be used in further chemical reactions for immobilizing DNA. Further, a light transmissive plastic such as polystyrene may be used for the DNA chip substrate. Various techniques known to those skilled in the art are included in the patents incorporated by reference, above, as well as in the following references, which are incorporated herein by reference: Laursen et al., "Solid Phase Methods in Protein Sequence Analysis Methods of Biochemical Analysis," vol. 26 John Wiley & Sons, Inc. 1980, pp. 202–215; "Immobilization of oligonucleotides onto a glass support via disulfide bonds: A method for preparation of DNA microarrays," Rogers Y H, Jiang-Baucom P, Huang Z J, Bogdanov V, Anderson S, Boyce-Jacino M T, Anal Biochem Jan. 1, 1999 266(1):23–30; "Covalent attachment of DNA oligonucleotides to glass," Cohen G, Deutsch J, Fineberg, J, Levine A, Nucleic Acids Res Feb. 15, 1997 25(4):911–2; "Hybridization of DNA targets to glass-tethered oligonucleotide probes," Beattie W G, Meng L, Turner S L, Varma R S, Dao D D, Beattie K L, Mol Biotechnol December 1995 4(3):213–25; "Preparation of glass plates with cerium oxide for DNA sequencing," Millard D, de Couet H G, Biotechniques October 1995 19(4): 576; "Biologically Functional Materials," Allan S. Hoffman, in Biomaterials Science, B. D. Ratner, A. S. Hoffman, F. J. Schoen, and J. E. Lemons, Eds., pp. 124–130.

Further, various embodiments of the present invention as described herein (e.g., bar code reader type embodiments)

may provide for imaging of DNA chips that are not light transparent, e.g., substrates that do not pass light. For example, such substrates may include various materials generally used to provide DNA chips. As such, depending upon the detection system configuration, a DNA chip may or may not need to be light transparent.

The invention may be used with DNA or with other combinations of hybridizable molecules, for instance RNA-DNA or DNA-protein interactions. DNA-DNA hybridization has been used as an example but the invention may be used with all polynucleic acid hybridization techniques, including RNA-RNA hybridization. As described previously herein, polynucleic acid, as used herein, means DNA, RNA, two or more oligonucleotides or oligonucleosides, and all long or short sequences of nucleic acids. A "DNA chip" or "polynucleic acid chip" as used herein is one type of biological sample that is generally classified as a type of micro-array. A DNA chip generally refers not only to DNA sequences immobilized on small solid substrates, but also refers to RNA, etc., and generally to any device, substrate, or other object with biomolecules immobilized thereto. However, a biological sample, as used herein, is clearly not limited to a DNA chip and refers to other types of biological samples such as 1-D and 2-D gels, etc.

FIGS. 3A–3B illustrate two alternative optical configurations for the image detection apparatus 101 for use in direct mapping according to the present invention. In FIG. 3A, the sampling surface 114 of the DNA chip 14 is in contact with a first side 115 of the optical filter 17. The second side 117 of the optical filter 17, i.e., the side opposite the first side 115, is in direct contact with a surface 119 of the detector 4 upon which the detector pixels 5 are located. As such, for example, excitation light transmitted through the substrate of the chip 14 excites the biological material on the sample surface 114 and any fluorescence is transmitted through the filter 17 to the detector pixels 5 of the detector 4, e.g., CMOS detector array.

One skilled in the art will recognize that the opposing surface 124, i.e., opposite the sampling surface 114, of the DNA chip 14 may be in contact with a first side 115 of the optical filter 17. In the imaging process, light emanating from the sample surface 114 of the chip 14 is then transmitted through the chip substrate to the detector pixels 5 of the detector 4, e.g., CMOS detector array.

In FIG. 3B, the DNA chip 14 is in sequence with a mapping lens 21. The sampling surface 114 of the DNA chip 14 is in direct contact with a first side 129 of the mapping lens 21. The second side 131 of the mapping lens 21, i.e., the side opposite the first side 129, is in direct contact with a first side 115 of the optical filter 17. The second side 117 of the optical filter 17, i.e., the side opposite the first side 115, is in direct contact with a surface 119 of the detector 4 upon which the detector pixels 5 are located. In the imaging process, light from the chip 14 is focused by the mapping lens 21 through the filter 17 to the detector pixels 5 of the detector 4, e.g., CMOS detector array. Preferably, the mapping lens 21 has a focal length suitable for focusing the light emitted by the chip 14 onto the detector pixels 5 of the detector 4. Yet further, the mappings lens may be a lens configured for collimating light impinging thereon. As in the embodiment of FIG. 3A, the opposing surface 124 of the DNA chip 14 may be in direct contact with the first side 129 of the mapping lens 21.

The theoretical resolving power of the image detection apparatus and methods described above will be directly related, at least in part, to the spacing between the DNA chip light emitting regions, e.g., the sampling surface 114 on which the nucleic acid spots are positioned, and the surface 119 upon which the imaging detector pixels 5 are located, i.e., the length of the light path. The actual resolving power will also be a function of the emission from the DNA spots and the sophistication of the software used to extract and reconstruct the light therefrom, e.g., the DNA fluorescence.

Further, the theoretical resolving power of the configuration including a simple mapping lens 21 or lens system will be limited by the optical quality of the mapping lens 21 and by light diffraction. However, it is not the goal of this system to have high cost resolution imaging optics as part of the present detection apparatus since low cost optics with suitable software will readily map arrays of DNA pixels.

The resolving power of direct mapping can be computed as the sum of: the larger of the detector pixel diameter (e.g., roughly 10 $\mu$m) or spot diameter; chip 14 thickness (e.g., 10 $\mu$m); and filter thickness (10 $\mu$m). Thus, the image from a 10 $\mu$m DNA spot (assuming the chip thickness and filter thickness are both about 10 $\mu$m) would map onto a 30 $\mu$m×30 $\mu$m area of the detector containing 9 detector pixels, while the image from a 50 $\mu$m DNA spot (assuming the chip thickness and filter thickness are both about 10 $\mu$m) would map onto a 70 $\mu$m×70 $\mu$m area containing 49 detector pixels. For example, a CMOS device such as the HDCS-1100 (Hewlett-Packard Components Group; Corvallis, Oreg.) which has a 352×288 detector pixel array, can resolve approximately 1,000 spots that are 10 $\mu$m in diameter, and approximately 2,000 spots that are 50 $\mu$m in diameter.

The detector pixels of suitable electronic light detector arrays may also integrate light emission with time, in much the same way that longer photographic exposure is used to develop faint images. This time integration will permit the detection of any light impulse that can be detected with a computer-assisted confocal microscope so long as the fluorescence signal exceeds detector dark current and background light.

Further, the optical system of the invention (for example, a single mapping lens) can magnify or reduce the image. A mapping lens would permit the emissions from the DNA chip to be optimally projected onto the detector pixels of a CMOS device. For instance, a reducing mapping lens may be capable of mapping the emission from a 50 $\mu$m spot onto an individual detector pixel.

FIG. 4 is a block diagram of a system substantially similar to that of FIG. 2, wherein light from a biological sample, such as a DNA chip 14 having biological material 13 thereon, is passed through an optical filter 17 and provided to detector pixels 5 of a detector 4, e.g., a CMOS or CCD detector, where such light is sensed. Signals representative of the sensed light may be digitized, relayed to computer 8, and subsequently processed and displayed as an image 18 on the computer's monitor 11. The image detection apparatus 101 of FIG. 4 may be modified with various light sources in various configurations thereof.

Figure 5:
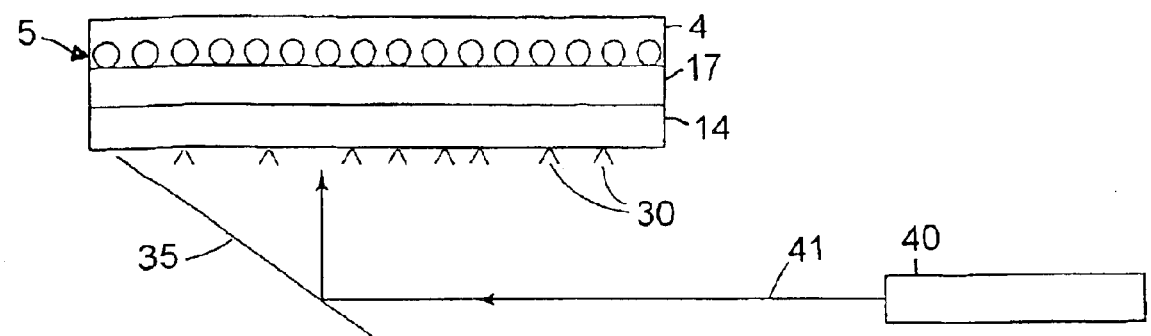
FIG. 5 illustrates an embodiment of an electronic light detector array detection system according to the present invention with a laser-light source.

For example, the system shown in FIG. 4 is compatible with laser-based visualization techniques as shown in FIG. 5. In other words, the image detection apparatus 101 of FIG. 4 may be modified to be in the configuration shown in FIG. 5. For instance, a laser 40 may be used to generate laser light 41 that may be reflected off of mirror 35 and thereby directed onto labeled DNA 30 hybridized and immobilized on DNA chip 14. In view of the incorporation of a fluorescent label, the hybridized DNA 30 fluoresces and emits fluorescent light upon excitation by the laser light 41. The filter 17 selectively passes the fluorescent light but not the laser light 41. The fluorescent light is directly mapped onto the detector pixels 5 of detector 4, e.g., a CCD detector array. The laser 40 may be rastered across the biological sample, e.g., the DNA chip 14, so that only select portions of the sample are illuminated at one time. The laser 40 may be, for example, laser diodes such as green (532 nm), red (635 nm), or far red (670 nm) diodes having a power in the range of 4 mW to 10 mW.

Figure 6:
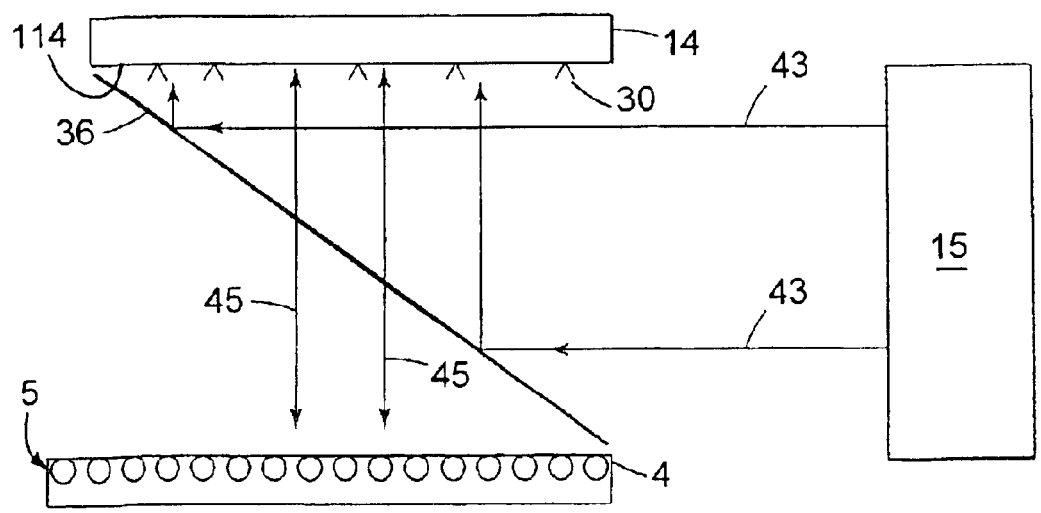
FIG. 6 illustrates an embodiment of an electronic light detector array detection system according to the present invention with a dichroic mirror.

The system of FIG. 4 may also use a lamp-type light source 15 as shown in the dichroic mirror arrangement of FIG. 6. As shown therein, the lamp-type source 15 emits light 43 that is reflected off a dichroic mirror 36 onto immobilized, labeled, and hybridized DNA 30. If the label on the hybridized DNA 30 is a fluorescent label, then the fluorescence emitted in response to excitation by light 43 may pass through dichroic mirror 36 and be mapped directly onto a detector 4, e.g., CCD detector array. An image representative thereof may be displayed on a computer monitor or stored in a computer memory using the techniques already described.

As shown in FIG. 6, direct mapping may still be accomplished even though the emitted light from the DNA spots is not provided through a light transparent DNA chip 14. In this embodiment, the biological material 30 is provided on a sample surface 114 that faces the dichroic mirror 36. The light from the sample surface 114 including the biological material 30 is filtered by the mirror 36 and impinges on the detector pixels 5 that are also facing the dichroic mirror 36. In other words, in this configuration, the detector 4 and biological sample, e.g., DNA chip 14, are separated by a dichroic mirror 36 that performs the filtering function. Further, the DNA chip 14 need not be transparent as the sample surface 114 is facing the detector pixels 5. In other words, the light path from the sample surface 114 to the detector pixels 5 is not through the substrate or biological material holding structure of the biological sample associated with the biological material.

Yet further, in some embodiments described herein, an excitation filter between a light source and the biological sample may be needed to filter out certain light from the light source that may interfere with the detection of certain light wavelength.

Figure 7:
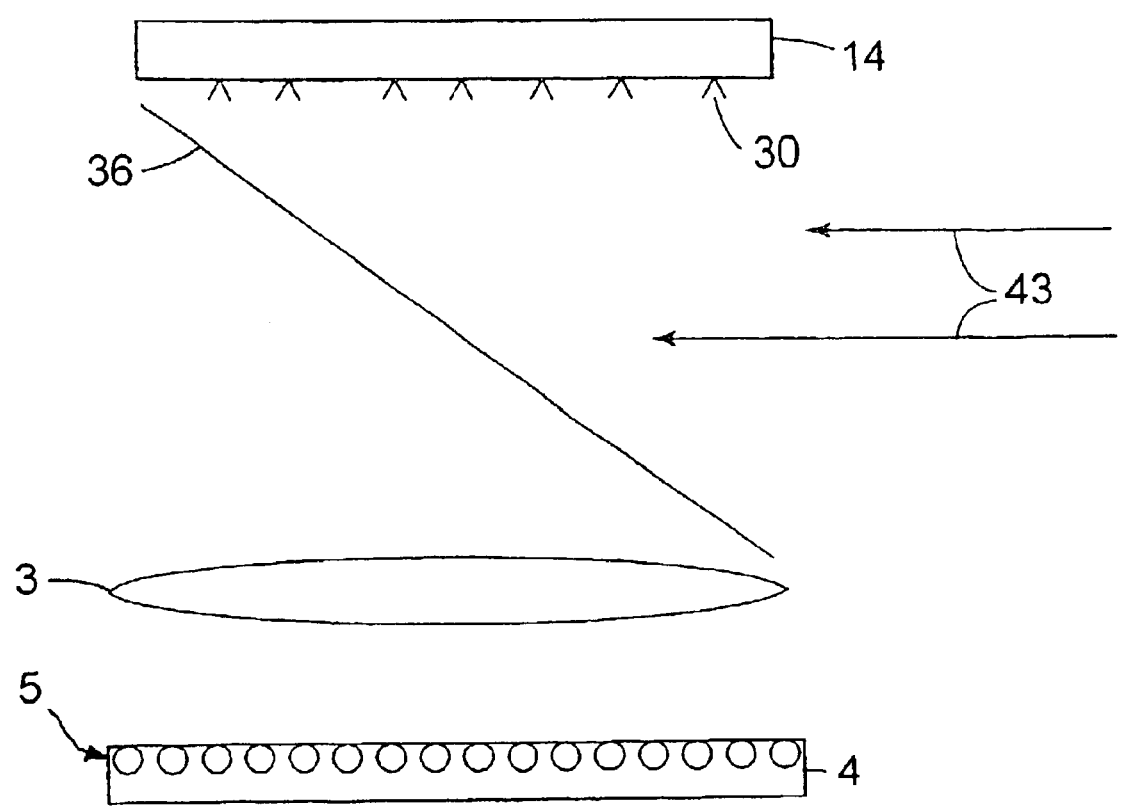
FIG. 7 illustrates an embodiment of an electronic light detector array detection system according to the present invention with a dichroic mirror and a mapping lens.

As shown in FIG. 7, a mapping lens 3 may be used to enhance the direct mapping of the system described above with reference to FIG. 6 incorporating a dichroic mirror 36. The mapping lens 3 will focus light that passes through dichroic mirror 36 such that DNA chip pixels of the DNA chip 14 are mapped onto one or more of the detector pixels 5 of detector 4, e.g., a CCD detector 4.

As an alternative arrangement to certain embodiments described herein, creation of a negative image may be performed. Numerous techniques and combinations of components for making negative images will be immediately apparent to those skilled in the art upon reading this disclosure. A few examples are provided herein but are in no way intended to limit the present invention. A negative image could be made by causing DNA to appear as a dark spot on a bright field. For instance, a bright fluorescent field, created by making the substrate of the DNA chip 14 with autofluorescent components, could be used with a label on hybridized DNA 30 that quenches or blocks light. The hybridized DNA would then appear as dark spots on a computer generated image. Compounds that quench fluorescence are known to those skilled in the art.

Alternatively, hybridized DNA could be labeled after it is immobilized to the DNA chip 14. For instance, a stain that blocks transmission of visible light may be used. Further, the DNA could already incorporate a label that could be calorimetrically developed after the DNA is immobilized, e.g., the hybridized DNA might have an enzyme that would cause a colored precipitate to form when the chip was exposed to a suitable substrate, such as, for example, a horse radish peroxidase (HRP) system could be used. Yet further, the immobilized DNA might have a fluorescent molecule that was quenched by elements on the hybridizing DNA.

Figure 8A:
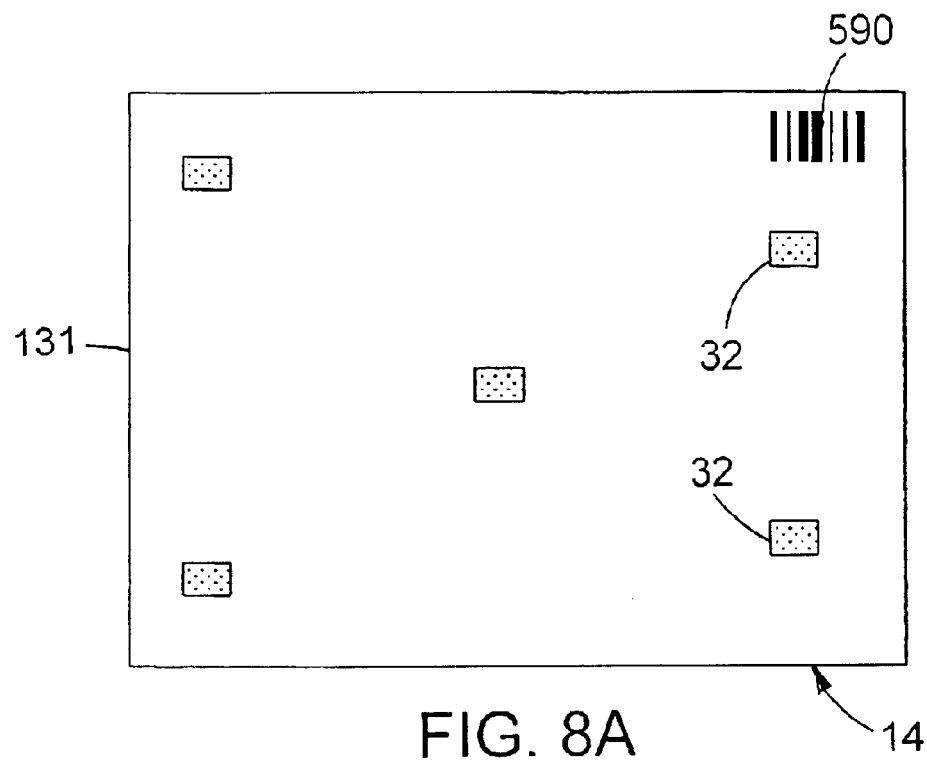
FIG. 8A illustrates a DNA chip with hybridized DNA to be mapped using an electronic light detector array detection system according to the present invention.
Figure 8B:
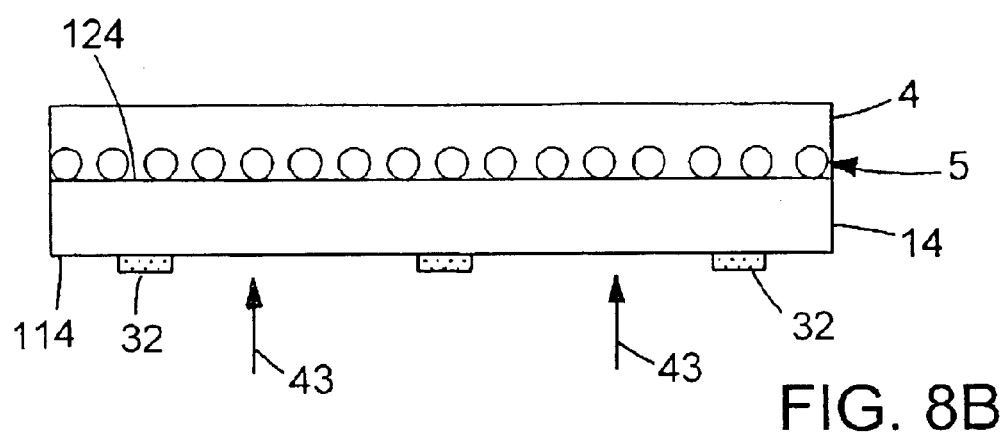
FIG. 8B illustrates an embodiment of an electronic light detector array detection system according to the present invention with no optical filter.
Figure 8C:
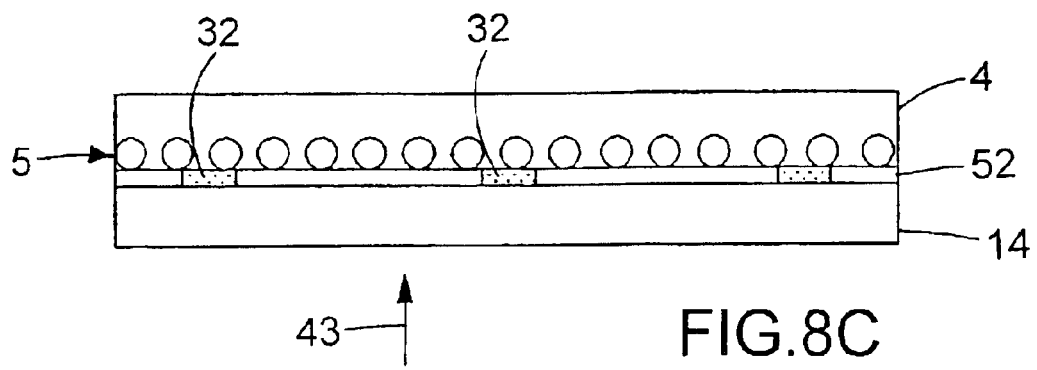
FIG. 8C illustrates an embodiment of an electronic light detector array detection system according to the present invention with a cover and no optical filter.

The previous embodiments described may be configured without an optical filter 17 as shown in FIGS. 8A–8C. For example, a light transmitting DNA chip 14 with hybridized DNA 32 on a biological material holding structure 131 as shown in FIG. 8A may be treated so that the hybridized DNA appears as dark spots that fully or partially block light. The DNA chip may then be positioned as shown in FIGS. 8B or 8C. As shown in FIG. 8B, the sample surface 114 is positioned opposite the detector pixels 5 of detector 4. In other words, the side 124 of DNA chip 14 opposing the sample surface 114 faces the detector pixels 5.

As shown in FIG. 8C, the sample surface 114 faces the detector pixels 5 of detector 4. In other words, the sample surface 114 of the DNA chip 14 is on the side opposite the light source 43. A cover 52 may be interposed between the sample surface 114 having the DNA spots 32 thereon and the detector pixels 5 so that detector 4 is not degraded by the DNA spots 32. The cover 52 may be a mere protective film such as a coating, or a coverslip, a plastic wrap such as polyethylene film, or any other material that transmits the wavelength of the light 43.

In the configurations shown in FIGS. 8B and 8C, light 43 (such as shown in the embodiment of FIG. 7) from a light source passes though DNA chip 14 but is blocked by light-blocking hybridized DNA 32. The resultant map that is formed on detector 4, e.g., a CCD detector array, shows the addresses that have hybridized DNA. Many fluorescent and non-fluorescent techniques for labeling DNA before or after its hybridization to DNA or before or after its immobilization to the DNA chip 14 are known to those skilled in these arts. Light 43 may be any wavelength specified herein as light and DNA 32 may be any means for blocking that transmission that is known to those skilled in the art.

It is noted that, in FIGS. 8B and 8C, no optical filter is used in the light path between the sample surface of the DNA chip 14 and the electronic light detector 4. All wavelengths of the source light 43 are allowed to reach the detector pixels 5 of the detector 4. However, a neutral density filter may be used in the light path between the sample surface and the detector 4. The neutral density filter may be used to block some of the source light 43 without filtering out any wavelengths of light.

Figure 9A:
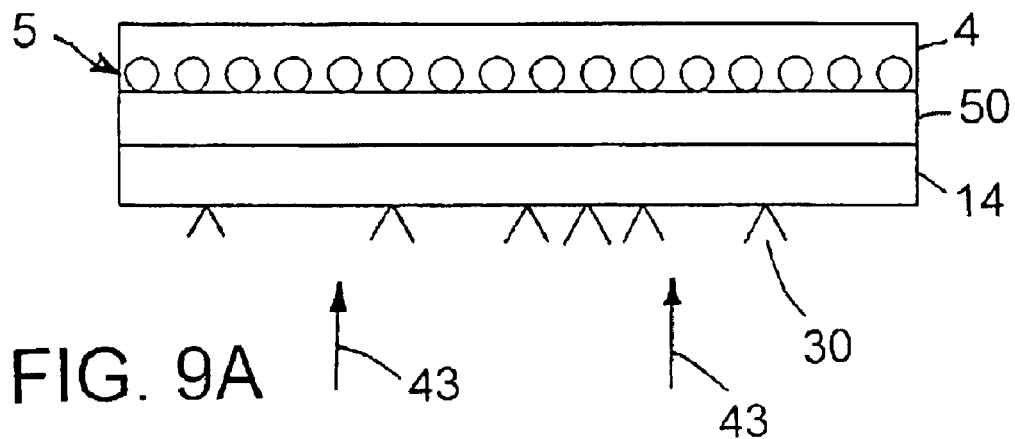
FIG. 9A illustrates an embodiment of an electronic light detector array detection system according to the present invention with a combination mapping lens-filter.
Figure 9B:
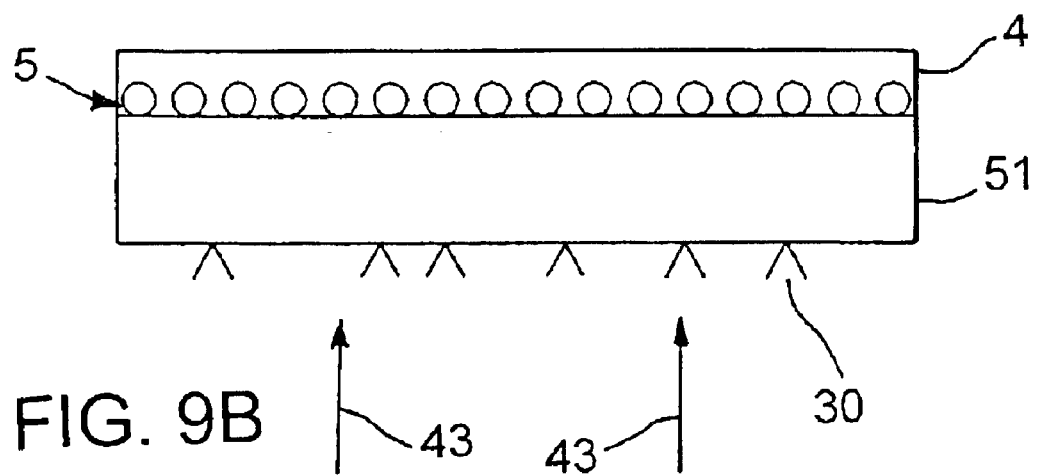
FIG. 9B illustrates an embodiment of an electronic light detector array detection system according to the present invention with a combination chip-filter.

The filters 17, lenses 3, and biological samples, e.g., DNA chips 14, shown in many of the embodiments described above may be used in various combinations as exemplified in FIGS. 9A and 9B. For example, a lens and filter may be combined into lens-filter 50 that is interposed between the DNA chip 14 and detector 4 as shown in FIG. 9A. Further, for example, the DNA chip 14 may be made as part of an integral single DNA chip-filter 51 that provides a solid substrate for DNA immobilization and acts to filter the light 43 from the light source or from the immobilized DNA 30 as shown in FIG. 9B. Materials or coatings used for filters are well-known to those skilled in the optical arts. The optical coating is generally formed on the surface of the chip 14 opposing the sample surface. In one embodiment, the optical coating allows passage of light wavelengths of fluorescence but substantially blocks other light wavelengths in the range of 300 nanometers to 600 nanometers.

Further, the DNA chip 51 may include an optical lens along with or in addition to the filter. For example, the surface of the DNA chip opposing the sample surface may be a curved surface that functions as a mapping lens. Preferably, the optical lens has a minium focal length of 10 microns and more preferably 5 microns. Further, preferably, the optical lens has a maximum focal length of 750 microns; more preferably, 400 microns; yet more preferably, 250 microns; and most preferably, 40 microns. Such focal lengths are applicable to the other embodiments using mapping lenses as described above.

Figure 10:
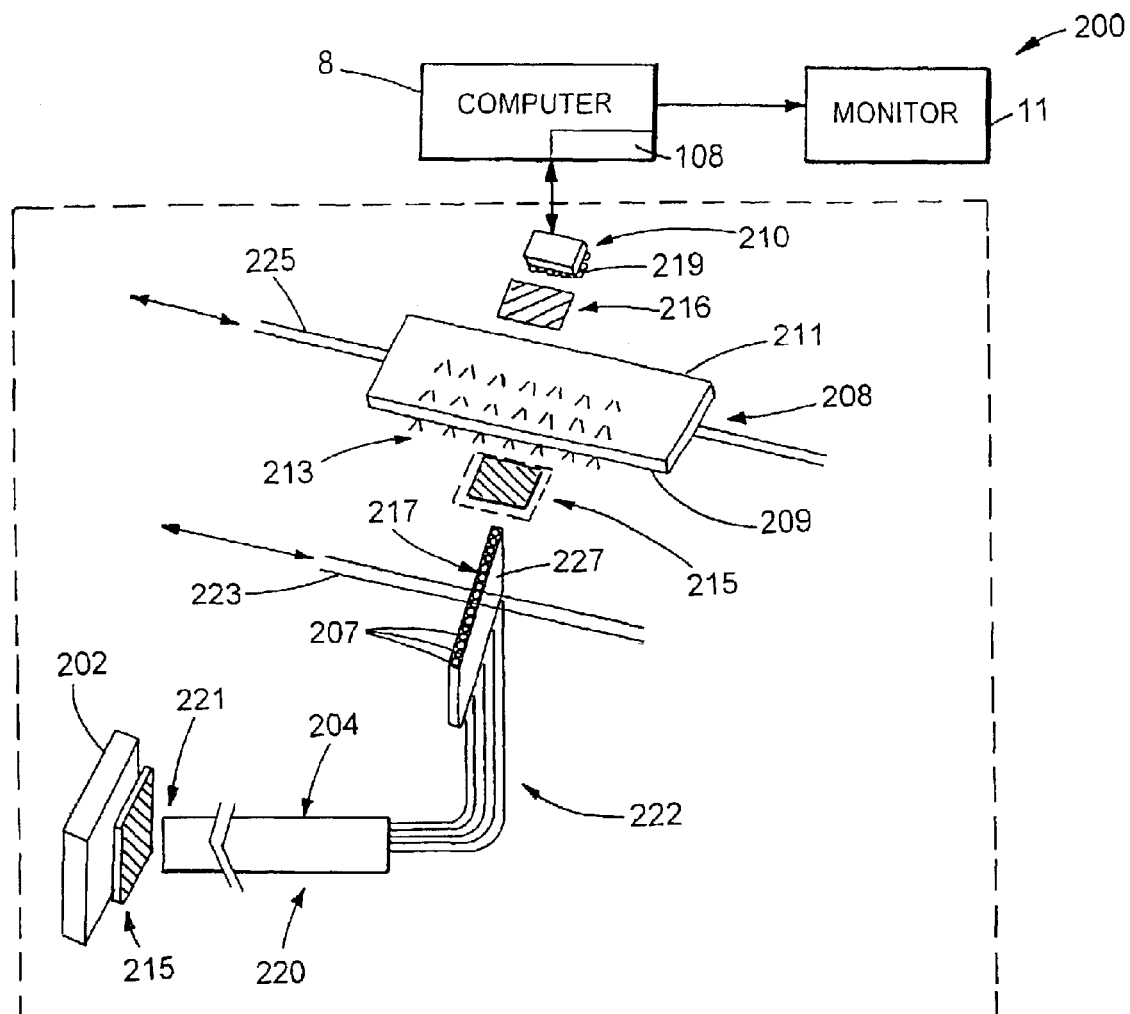
FIG. 10 shows another alternate embodiment of an image detection apparatus according to the present invention.

FIG. 10 shows another alternate embodiment of an image detection apparatus 201 according to the present invention. The image detection apparatus 201 may be referred to as a lens-free transmission light microscope as no lenses are necessary to perform the desired imaging. For example, the microscope or image detection system 200 may be used to resolve images with features as small as 10 μm in diameter. The image detection apparatus 201 is a transmissive imaging configuration as the configuration provides for detection of light from a biological sample 208 which has biological material 213 on a sample surface 209 thereof, and which requires the use of transmitted light through all, or at least a major portion of, the biological material holding structure 211, e.g., DNA chip substrate, gels that may be associated with a substrate or imaged alone, etc.

In other words, at least in the embodiment shown in FIG. 10, the transmitted light from a fiber optic bundle 220 illuminates or excites the biological sample 208, e.g. a light absorbing sample or a fluorescent producing sample. Light from the biological sample 208 then travels through the light path that includes the biological material holding structure 211 of the biological sample 208 to impinge on the electronic light detector 210. In other words, for the electronic light detector 210 to detect light from the biological sample 209, light is passed through or transmitted through the biological holding structure of the biological sample 208. In this embodiment, the biological holding structure of the biological sample 208 must be light transmissive structure, e.g., glass, clear materials, or other materials that permit transmission of suitable or desirable wavelengths of light.

The detection system 200 of FIG. 10 generally includes a light source 202, polarizing filters 215–216, a fiber optic bundle apparatus 220, an electronic light detector and associated circuitry 210 (e.g., CCD array or CMOS array), a computer 8 having memory 108 for use in storing any necessary software for carrying out the present invention and/or for analyzing any image data from the image detection apparatus 201, and a monitor 11 or some other output device for interfacing with a user. In general, parallel light rays are produced that are passed perpendicular to sample surface 209 of the biological sample 208, e.g., a microscope slide having, for example, light absorbing biological material or fluorescence producing biological material thereon. A transmission pattern of light through the biological material holding structure 211, e.g., the light transparent slide, is acquired by the electronic light detector 210 and captured by suitable image acquisition software associated with the detector 210 to produce image data. The image data may be provided for display on monitor 11 using computer 8.

In further detail with reference to FIG. 10, the light source 202 provides light that impinges on the first polarizing filter 215. Optionally, the light from the light source 202 may impinge on a receiving end 221 of the fiber optic bundle apparatus 220 as the first polarizing filter 215 may optionally be positioned between the fiber optic array 217 and the biological sample 208 instead of between the light source 202 and the fiber optic bundle apparatus 220. A second polarizing filter 216 that is orthogonal or 90 degrees rotated from the first polarizing filter 215 is positioned between the biological sample 208 and the electronic light detector 210. The polarizing filters are linear polarizers that prevent the electronic light detector 210 from oversaturation. Such oversaturation may reduce the dynamic range of the detector 210. Further, the polarizing filters 215–216 provide for the filtering of zero order diffraction in the system. The light source 202 may be any suitable light source such as a clustered white LED light source, a tungsten filament, or any other light source previously described herein.

The polarizing filter 215, if positioned between the light source 202 and the fiber optic bundle apparatus 220, provide the polarized light onto the receiving end 221 of the fiber optic bundle apparatus 220. The fiber optic bundle apparatus 220 generally includes the receiving end 221 of a bundle portion 204. The bundle portion 204 is then fanned out in a fanout bundle portion 222 and terminated at a fiber optic array portion 217, e.g., a one-dimensional (in-line or linear) array. For example, the fiber optic array portion 217 may include termination fiber ends 207 of individual fibers 205 positioned separately in openings of a fiber optic array holder 227 (shown in further detail in FIG. 11). The fiber optic array portion 217 provides for the illumination of the biological sample 208.

Light transmitted through the biological sample 208, e.g., the biological sample holding structure 211 associated with biological material 213 thereof, impinges on detector pixels 219 of the electronic light detector 210 and an image is detected representative of the biological material 213 of the biological sample 208. For example, if the biological sample 208 is a micro-array having fluorescent tagged nucleic acids thereon, then fluorescence would be transmitted through the light transparent micro-array substrate, onto the electronic light detector 210 (in this case, an emission filter may be required to prevent transmission of the excitation light from the fiber bundle from reaching the electronic light detector). Further, for example, if the biological sample 208 is a silver-stained DNA micro-array or chip, then such a light absorbing biological sample will absorb light and a transmission pattern representative of the light absorbed at particular locations will be transmitted through the substrate or holding structure of the DNA chip. The transmitted pattern will then be acquired by the electronic light detector 210.

Figure 11A:
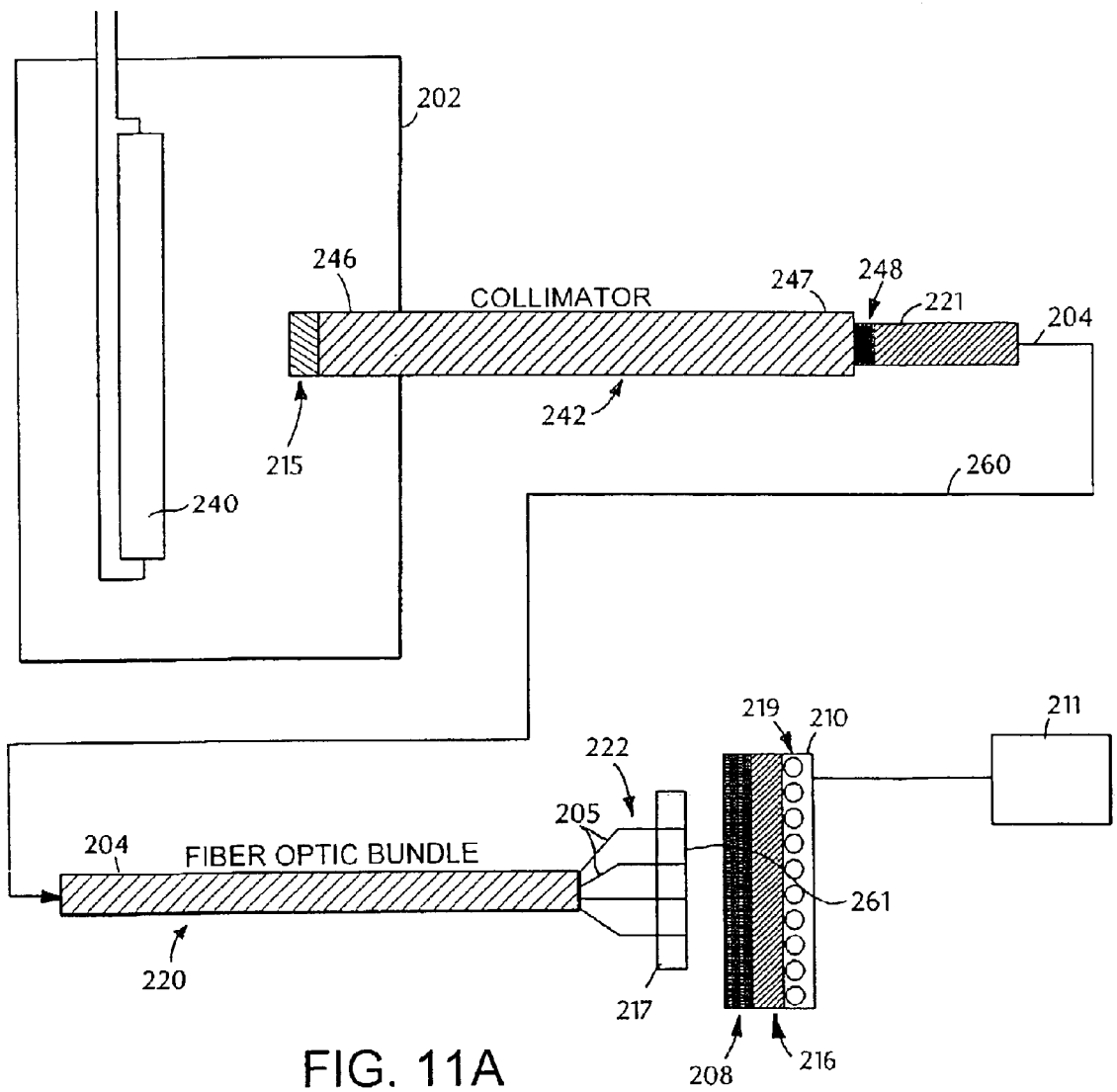
FIGS. 11A–11C provide an illustrative exemplary and more detailed configuration of the image detection apparatus generally shown in FIG. 10.

The biological sample 208, the polarizing filter 216 and the electronic light detector 210 may be positioned in any suitable manner as previously described herein such as shown in FIGS. 2–5 and 8–9. For example, as shown in the embodiment of FIG. 11A, the biological sample 208, polarizing filter 216, and the electronic light detector 210 are in direct contact with one another, with the electronic light detector 210 separated from the biological sample only by the thickness of the polarizing filter 216, which may, for example, have a thickness of about ½ millimeter. Preferably, the biological sample 208 and the detector pixels 219 of the electronic light detector 210 are as near one another as possible, at least in this particular embodiment. However, in no manner is the present invention limited to configurations that have one or more of the above elements, e.g., biological sample 208, the polarizing filter 216 and the electronic light detector 210, in direct contact. For example, the present invention may be employed with such elements in close proximity to one another.

Generally, in operation, the fiber optic array portion 217, e.g., a linear array of optical fibers, is scanned across the biological sample 208 using known scanning mechanics 223 generally represented in FIG. 10. For example, such scanning mechanics may include mounting structures, stepper motors, piezo-electric actuating elements, etc. Such movement may be controlled by a computer 8 under command of suitable software in memory 108. The present invention is not limited to any particular movement mechanics 223 as any scanning mechanics, at least in this particular embodiment, that can provide for linear movement will be suitable.

In other words, the linear array 217 of fibers is scanned across a stationary biological sample 208 such that the transmitted light from the biological sample 208 resulting from the illumination thereof is provided to one or more detector pixels of the electronic light detector 210. As such, a corresponding array of detector pixels, e.g., one or more detector pixels per fiber, detect light from the biological sample 208. A suitable image acquisition software program, such as a stitching program, may then be used to provide for combination of the scanned and detected captured image data to present a composite image data file that may be displayed or otherwise provided as output to the user. For example, image data from multiple arrays of detector pixels representative of portions of the biological sample 208 acquired during a scan of the biological sample 208 by the fiber array 217 may be combined to form a complete image of the biological sample 208.

Alternatively, the biological sample 208 may be moved by movement mechanics 225 such that image data representative thereof can be captured. In other words, with the fiber optic array 217 and the electronic light detector 210 held stationary, the biological sample 208 is moved such that the light from the individual fibers 205 of the array 217 impinge sequentially upon different linear portions of the biological sample 208 as it is moved. At each of the linear portions, light is detected, e.g., at an array of detector pixels or on a single linear array of pixels, from the biological sample 208. Upon capture of all desired linear portions thereof, suitable image acquisition software is used to combine the detected linear portions into a composite image data file representative of the biological sample 208, or at least a portion thereof.

Although use of a linear electronic light detector, e.g., a linear CCD, is possible, preferably, the light from the biological sample impinged upon by light from a single fiber is mapped to more than one detector pixel so as to provide more data for combining detected linear portions of the sample. In other words, with more pixel data available for each corresponding illumination fiber end 207, a sharper image can be created.

Figure 11B:
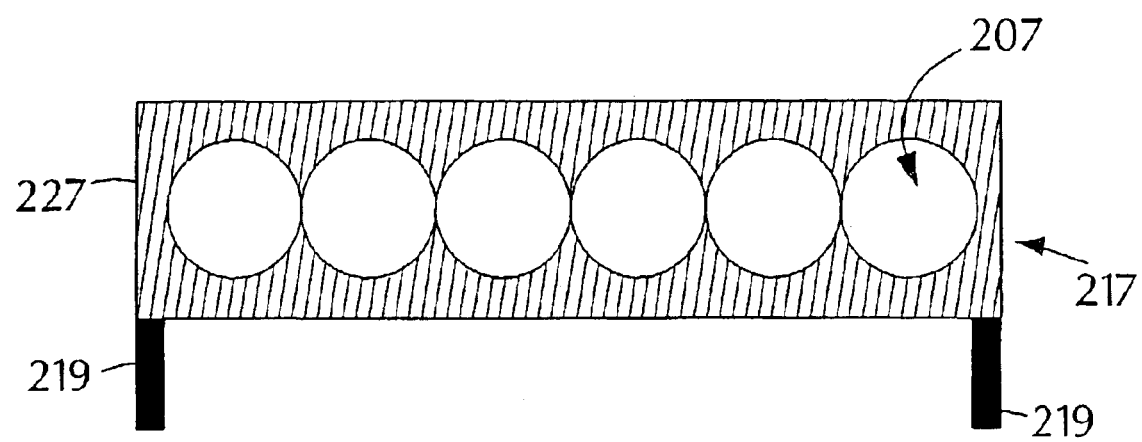
Figure 11C:
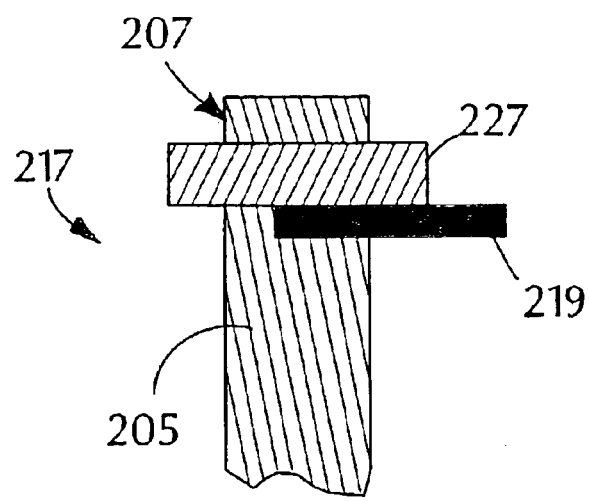

FIGS. 11A–11C provide an illustrative exemplary and more detailed configuration of the image detection apparatus 201 of the detection system 200 generally shown in FIG. 10. The detection apparatus 201 generally includes a light source 202, polarizing filters 215–216, a fiber optic bundle apparatus 220 (shown in two sections in FIG. 11A connected by line 260), an electronic light detector 210 and associated image acquisition circuitry 211 (e.g., CCD array or CMOS array and associated hardware and software). As shown in FIG. 11A, the light source 202 includes a clustered white LED array 240 that provides light that impinges on the first polarizing filter 215. The first polarizing filter 215 is positioned adjacent to a collimator 242. As such, light polarized by the filter 215 is provided through the collimator 242. For example, the collimator may be a long tube or any other type of collimator used by those in the art, such as an optical pipe capable of collimating the light.

The collimator 242 is attached for provision of light therefrom to the receiving end 221 of a fiber optic bundle portion 204 of the fiber optic bundle apparatus 220 using a coupling 248, such as a grommet. The bundle portion 204 is then fanned out into a fanout bundle portion 222 or individual fibers 205 with each fiber terminated at a fiber optic array portion 217, e.g., a one-dimensional (in-line or linear) array. The fiber optic array portion 217 includes termination fiber ends 207 of individual fibers 205 positioned separately in openings of a fiber optic array holder 227 as shown in FIG. 11B. The fiber optic array portion 217 provides for the illumination of a linear portion of the biological sample 208.

As described above with reference to FIG. 10, the biological sample 208, the second polarizing filter 216, and the electronic light detector 210 can be provided in numerous configurations. As shown in FIG. 11A, the biological sample 208, polarizing filter 216, and the electronic light detector 210 are in direct contact with one another, with the electronic light detector 210 separated from the biological sample 208 only by the thickness of the polarizing filter 216. The second polarizing filter 216 is orthogonal or 90 degrees rotated from the first polarizing filter 215 such that suitable filtering of at least zero order diffraction in the system is provided.

Light transmitted through the biological sample 208, e.g., the biological sample holding structure associated with biological material thereof, impinges on detector pixels of the electronic light detector 210 and an image is detected representative of the biological material 213 of the biological sample 208. The image is captured using suitable image acquisition circuitry and software 211 such as described above, e.g., image combining software. For example, such software and/or hardware may include software that can patch together the portions using overlapping information to provide additional resolution, such portions may be pieced together through storage individually in memory, etc.

As shown in the plan view of the face 261 of the fiber optic array portion 217 in FIG. 11B, individual fibers 205 terminate at fiber ends 207. Each fiber 205 is terminated in a corresponding opening of a fiber optic array holder 227. The fiber optic array holder 227 is associated with brackets 219 for connection to a stepper motor for movement to be controlled by computer 8 under command of suitable software.

FIG. 11C is a side view of the fiber optic array portion 217 shown in FIG. 11B. As shown therein, the individual fibers 205 terminate at ends 207 after insertion through openings in the holding structure 227. As previously described above with reference to FIG. 10, the fiber optic array portion 217 is scanned across the biological sample 208 and image data representative thereof is captured. For example, as the fiber optic array portion 217 is scanned across linear portions of the biological sample 208, the electronic light detector captures light from such linear portions. Thereafter, such detected linear portions may then be combined to form a composite image of the biological sample 208.

As previously described herein, reflective imaging configurations refer to configurations that provide for detection of light from a biological sample, e.g., a sample surface at which biological material is associated, which does not require the use of transmitted light through the biological holding structure of the biological sample, or a major portion thereof, e.g., DNA chip substrate, micro-titer plates, gels that may be associated with a substrate or imaged alone, etc.

Preferably, in a reflective imaging configuration, light (whether excitation, fluorescence, or reflected light from a biological sample) does not pass through the biological holding structure of the biological sample, or at least does not pass through a major portion thereof. In such cases, the biological holding structure need not be light transparent structure, but rather can be opaque materials, e.g., nitrocellulose, charged nylon, silicon as a substrate for micro-array formation, etc., which have more favorable properties than light transparent structure (e.g., glass).

Figure 12:
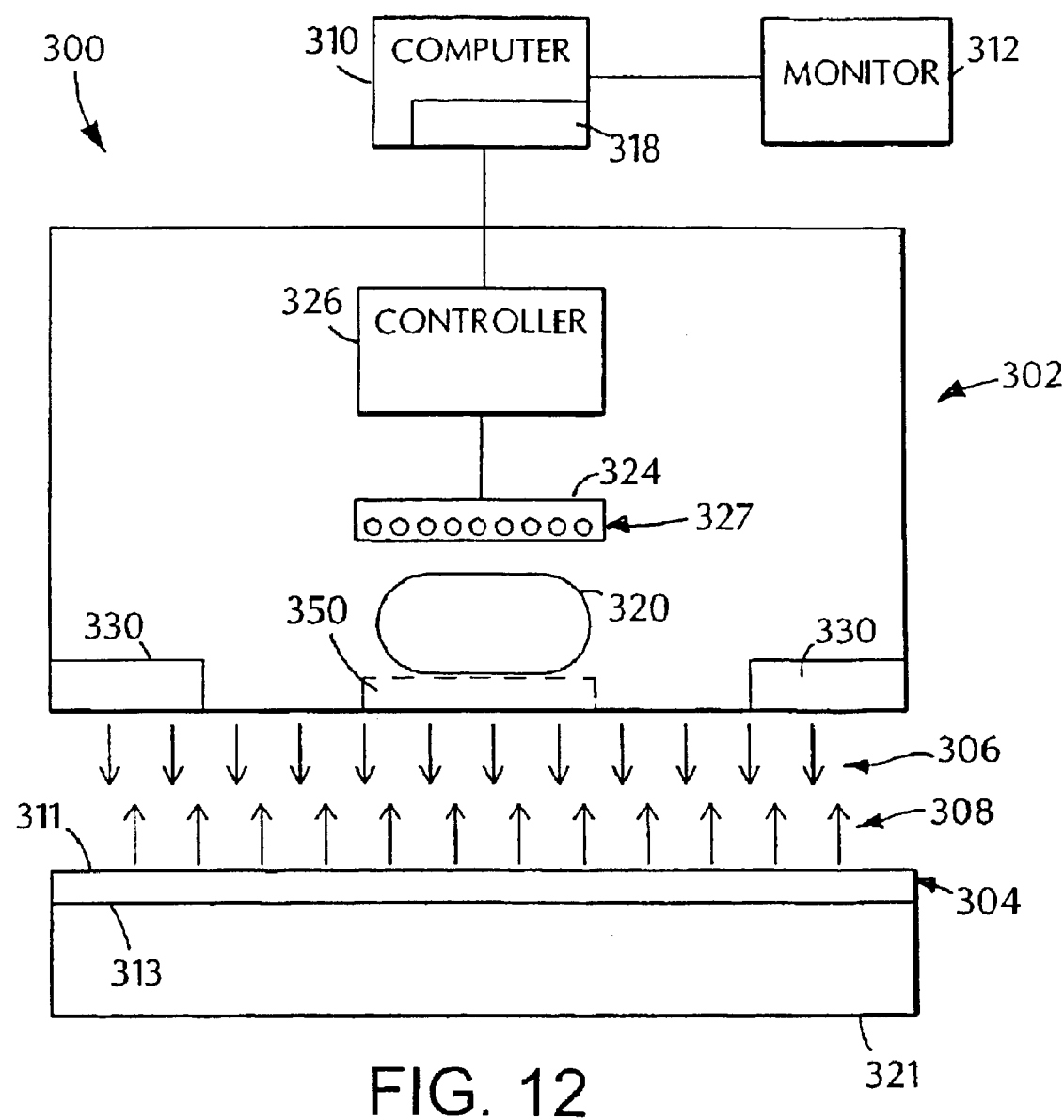
FIG. 12 shows an illustrative diagram of another alternate electronic light detector array detection system according to the present invention.

Such a reflective imaging configuration is shown by the electronic light detector array detection system 300 generally shown in FIG. 12. The electronic light detector array detection system 300 generally includes an image detection apparatus 302 for capturing one or more frames of an image, e.g., image data, preferably in digital form, representative of a biological sample 304 held in a stationary location (e.g., sampling position) by positioning structure 321. The image data is then provided to a computer 310 for reconstruction, storage in memory and/or analysis thereof. For example, the image data may be mapped to the computer memory 318 and processed to provide data representative of a reconstructed image for display on a monitor 312, e.g., a computer display or any other display apparatus that may display image data representative of the reconstructed image. Such reconstruction may use one or more frames of image data.

The positioning structure 321 may be any structure or mechanisms available for maintaining the biological sample 304 in a fixed position. For example, the positioning structure may include clamps, clips, wells, adhesives, etc. Further, such positioning structure may include movement mechanisms for moving the biological sample 304 into multiple sampling positions and locking the sample into the fixed sample position. For example, such movement may be used to focus an image as previously described herein.

The image detection apparatus 302 generally comprises a light source 330 located for providing light 306 (e.g., excitation light or illumination light) onto the biological sample 304, or at least a portion thereof. Further, the image detection apparatus 302 comprises an electronic light detector 324 and a lens 320 for focusing light 308 (e.g., fluorescence or reflected light) from the biological sample 304 onto detector pixels 327 of an electronic light detector 326. The electronic light detector 324 is operable under control of control circuitry 326, e.g., a frame grabber. For example, the control circuitry 326 receives the sensed signals from the electronic light detector 324 and captures one or more frames of images to be used for later processing and/or display. Further, optionally, in the situation where the image detection apparatus 302 is used for detecting fluorescence as further described below, the image detection apparatus 302 also includes an interchangeable emission filter 350.

The image data may then be provided by the image detection apparatus 302 to a port of the computer 310. The image data may then be operated on by graphics manipulation software to, for example, reconstruct the image data and display a visual image on the monitor 312. Various types of software may be used. For example, QuickView (a Windows® application program) may be used to capture, save and categorize images and ImagePro Plus available from Media Cybernetics may be used for manipulation of graphics, etc.

Generally, the image detection apparatus 302 may be provided using a modified bar code reader such as a bar code reader available under the trade designation of WelchAllyn IMAGETEAM 4710HD/HD10 handheld or fixed mount 2D image reader. For example, the light source of the available 2D image reader may be modified to provide a light source as further described below and an emission filter may be added for use in fluorescent marker applications.

The image detection apparatus 302 may be used to image fluorescence, e.g., detect fluorescent probes or markers bound to specific locations on DNA chips such as in genomics research or fluorescent labeled proteins separated by two-dimensional gel electrophoresis such as in proteomics research. For example, biological samples 304 of considerable size, such as in the case of 2-D gels which can be relatively large (e.g., 25.4 cm×25.4 cm) can be imaged successfully. For example, preferably, with use of reducing lenses, biological samples 304 as large as 50 cm×50 cm may be imaged.

With respect to imaging fluorescence and with reference to FIG. 12, the biological sample 304 provides biological material including fluorescent markers associated with a biological material holding structure, e.g., a gel or a micro-array such as a DNA chip. For example, such biological material including the markers may be at particular addresses of the micro-array that correspond to addresses of one or more detector pixels. Excitation light 306 is directed onto the sample surface 304 to excite the fluorescent markers or cause excitation events that produce fluorescent light photons of characteristic wavelength. Such fluorescent light 308 is passed through the lens 320, focused and projected as an image representative of the fluorescence from the excited sample onto the detector pixels 327 of the electronic light detector 324. The excitation light reflected by the sample surface 311 is prevented from reaching or is blocked from the electronic light detector 324 and lens 320 by the emissions filter 350. The electronic light detector 324, e.g., a two-dimensional array detector, under control of circuitry 326, grabs a frame of the fluorescence image and provides the image data for reconstruction alone, or more preferably in combination with one or more other frames of image data.

With respect to imaging reflected light, i.e., representative of the absorption characteristics of the biological sample 304, and with reference to FIG. 12, the biological sample 304 provides biological material that for example, may be stained or otherwise detectable such as with the use of color, density, etc. The biological material is associated with a biological material holding structure, e.g., a gel or a micro-array such as a DNA chip. Illumination light 306 is directed onto the sample surface 311 of the biological sample 304. Based on the absorption and reflective characteristics of the biological sample 304, reflected light is passed through lens 320 and is focused and projected as an image representative of the biological sample 304, e.g., stained or colored portions thereof, onto the detector pixels 327 of electronic light detector 324. The electronic light detector 324, e.g., a two-dimensional array detector, under control of circuitry 326, grabs a frame of the reflected image and provides the image data for reconstruction alone, or more preferably in combination with one or more other frames of image data.

Although the image detection apparatus 302 can be used to produce images from various biological sample configurations that use, for example, single color fluorescence, multiple color fluorescence, chemi-luminescence, chemi-fluorescence, calorimetric detection, densitometry, or any other technique detectable through imaging, the present invention is particularly beneficial for fluorescence imaging. As such, the remainder of the description below shall be provided with respect to such fluorescence imaging.

For example, the image detection apparatus 302 may be used for rapid production of single-color and multi-color fluorescence images, e.g., images showing fluorescent positions such as regions, spots, areas, etc., of a biological sample (e.g., fluorescent positions on a micro-array or DNA chip) when such material is caused to fluoresce by an excitation light or by chemi-fluorescence. As described previously herein, a wide range of samples, including, but not limited to gels, blots, micro-arrays, micro-plates, etc. may be imaged to detect fluorescent positions. The use of a modified bar code reader as presented herein provides methods and systems that have a high sensitivity for detection of flourescent dyes and labels, including, but clearly not limited to, ethidium bromide, SYBR® Green, SYBR® Gold, SYPRO®, Radiant Red, fluorescein (FITC), rhodamine, Cy2, Cy3, Texas Red, Green Fluorescent Protein.

The modified bar code reader or image detection apparatus 302 provides multi-mode imaging with the ability to select multiple wavelength light excitation, epi-illumination, or optionally transmittance illumination. Multiple frames may be grabbed for a single biological sample over time providing for improved image resolution and uniformity. Further, as previously described herein, the imaging area of the biological sample 304 is comparatively large relative to other detection systems.

Figure 13:
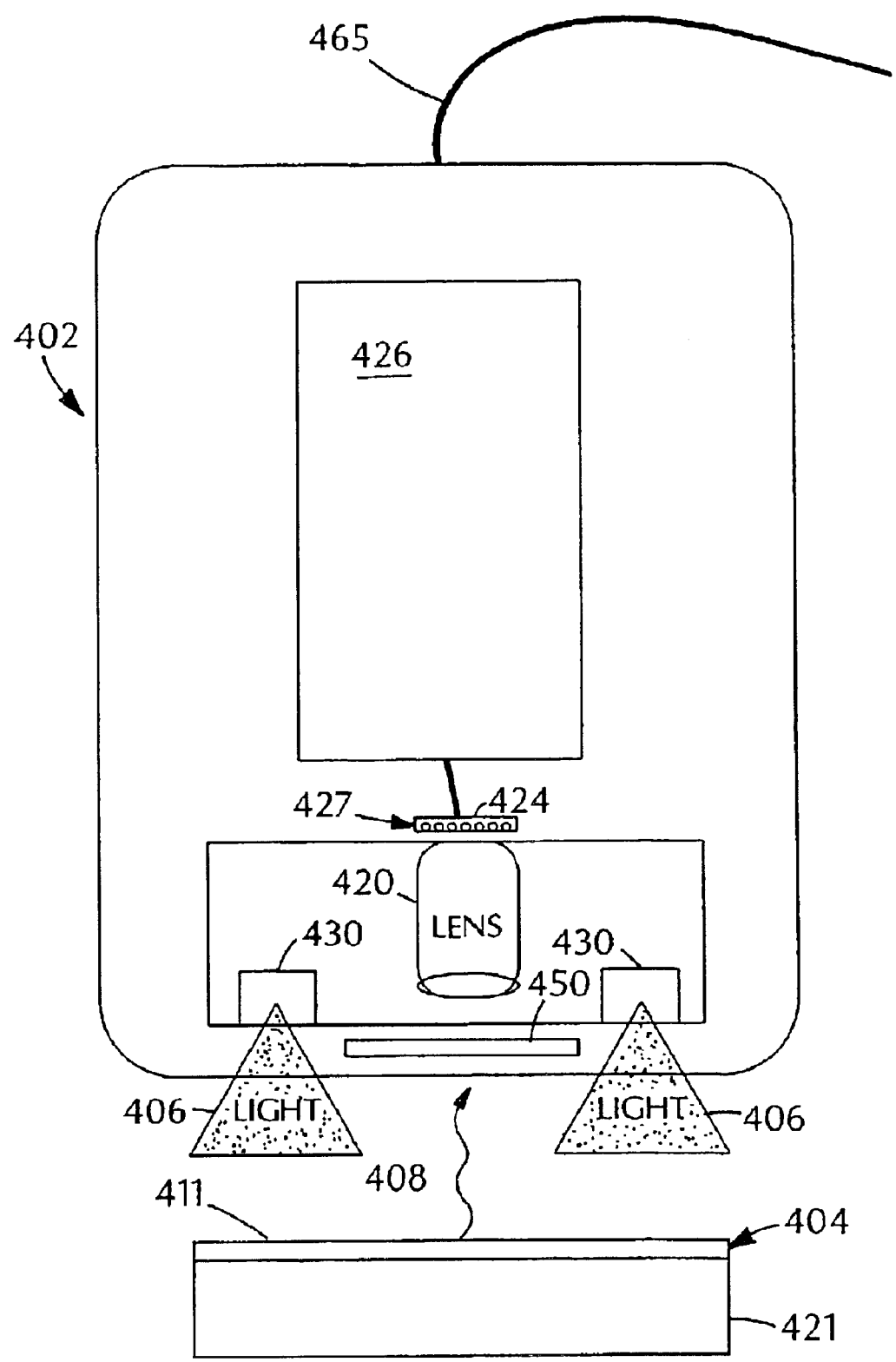
FIG. 13 shows one illustrative exemplary and more detailed configuration of the image detection apparatus of the system generally shown in FIG. 12.
Figure 14:
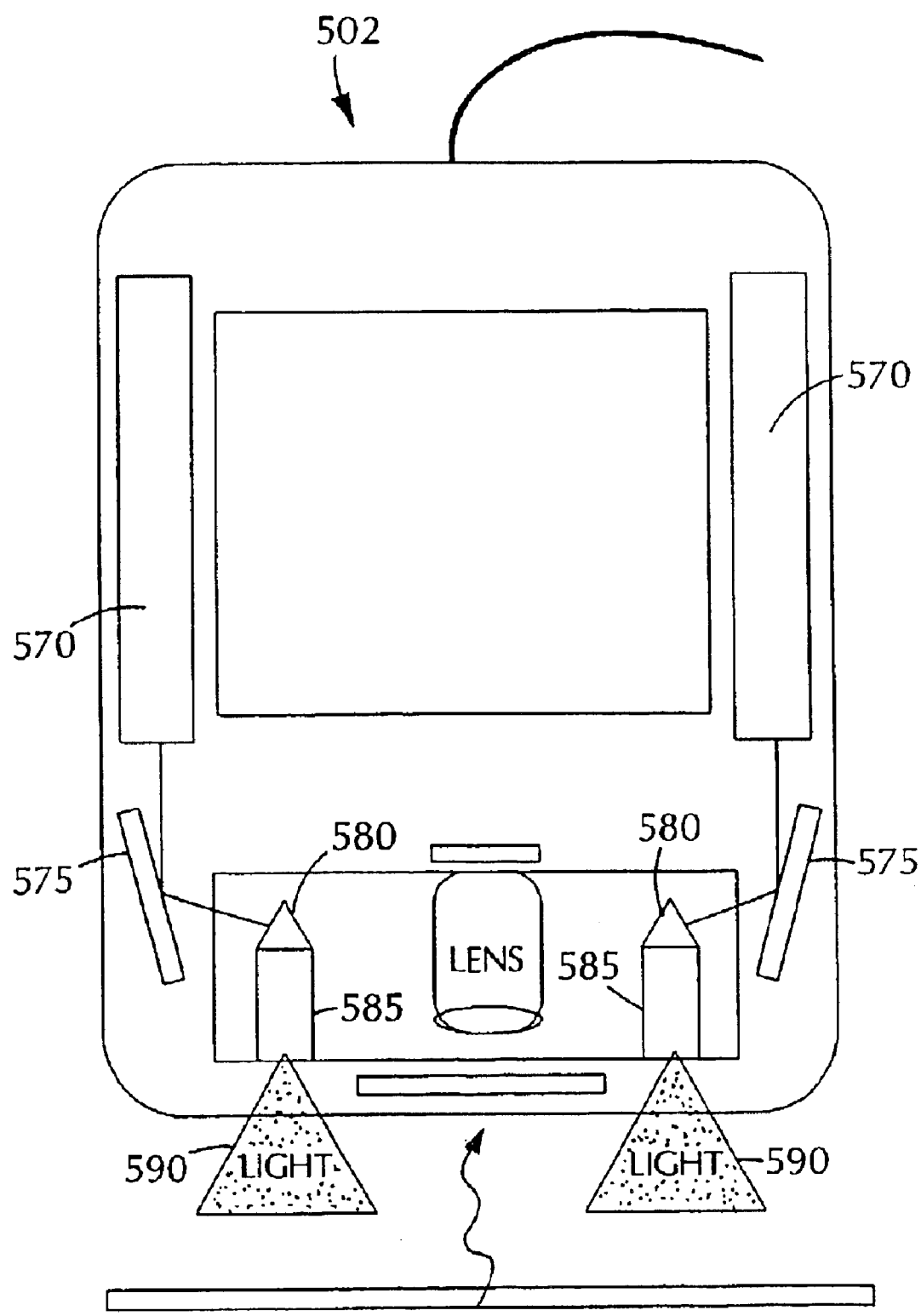
FIG. 14 shows another alternate illustrative exemplary and more detailed configuration of the image detection apparatus of the system generally shown in FIG. 12.

Two illustrative and exemplary image detection apparatus 402, 502, e.g., modified bar code readers, are shown in FIGS. 13 and 14, for use in fluorescence imaging. The image detection apparatus 402 differs from the image detection apparatus 502 in that the light source used for excitation is different. Each of the configurations employs a modified WelchAllyn IMAGETEAM 4710HD 2D image reader, although various other bar code readers may be modified as would be readily recognized from the description herein.

As shown in FIG. 13, the image detection apparatus 402 provides for capturing one or more frames of a fluorescence image, e.g., image data, preferably in digital form, representative of a biological sample 404 held in a stationary location by positioning structure 421, e.g., any structure or mechanisms available for maintaining the biological sample 404 in a fixed position. The image data may be provided to a computer for reconstruction, storage in memory and/or analysis thereof such as, for example, by way of a cable interface 465 to a serial port of a computer, or alternatively to a universal serial bus (USB). Various other manners of transmitting image data, such as with the use of frame grabber techniques, may be used, e.g., wireless techniques, parallel transmission techniques, etc. The image data may be mapped to computer memory and processed to provide data representative of a reconstructed image for display on a monitor, e.g., a computer display or any other display apparatus that may display image data representative of the reconstructed image such as previously described herein. The image detection apparatus 402 includes LEDs 430 for providing excitation light 406 onto the biological sample 404, or at least a portion thereof, e.g., the sample surface 411. For example, any number of LEDs may be used for providing any desired and suitable wavelength of light necessary for causing the desired fluorescence from the biological sample 404. In one preferred embodiment, three different wavelengths of light, e.g., 480 nm, 570 nm, and 660 nm light, are provided from 50 mW LEDs. For example, four LEDs of each wavelength may provide enough excitation light 406 for imaging a DNA chip or a 2-D gel. The wavelengths of light correspond to the particular fluorescent markers used. For example, the 570 nm light provides excitation of Cy3 fluorescent labels and the 660 nm light provides excitation of Cy5 fluorescent labels. One skilled in the art will recognize that various other excitation wavelengths can be incorporated into the detection apparatus depending upon the types of flourescent markers used.

Further, the image detection apparatus 402 comprises an electronic light detector 424 and a lens 420 for focusing fluorescence from the biological sample 404 through the light path onto detector pixels 427. The electronic light detector 424 may be any two dimensional light detector, e.g., CCD detector array or a CMOS array. Preferably, according to this particular illustrative embodiment, the electronic light detector 424 is a black/white CCD having the dimensions of ⅓ inch by ½ inch. The detector pixels 427 of the electronic light detector 424 face the sample surface 411 of the biological sample 404.

The electronic light detector 424 is operable under control of control circuitry 426, e.g., such as the circuitry provided in a WelchAllyn IMAGETEAM 4710HD 2D image reader. For example, the control circuitry 426 may include a frame grabber for capturing images sensed at a particular time by the CCD array 424, a DC convertor for providing power to the LEDs 430 and the CCD 424, as well as other processing circuitry capable of reading bar codes. Such bar code processing capabilities may provide a way of biological sample archiving as described further below.

Further, the image detection apparatus 402 also includes an interchangeable emission filter 450. The emission filter 450 is configured and positioned to filter or block the excitation light or reflected excitation light 406 from the electronic light detector 424. As such, the excitation light is prevented from reaching the electronic light detector 424.

In operation, for example, with a biological sample 404 that is a gel or DNA chip tagged with the fluorescent markers Cy3 and/or Cy5, excitation light 406 is directed onto the sample surface 404 to excite the fluorescent markers such that fluorescence 408 is produced having certain wavelengths not block from the CCD array 424 by emission filter 450. Such fluorescence 408 is passed through lens 420 and is focused and projected as an image representative of the fluorescence from the excited sample onto the detector pixels 427 of CCD array 424. The excitation light reflected by the sample surface 411 is prevented from reaching or is blocked from the CCD array 424 by the emissions filter 450. The CCD array 424 under control of control circuitry 426 grabs a frame of the fluorescence image and provides the image data for reconstruction alone, or more preferably in combination with one or more other frames of image data representative of the biological sample 404.

The distance of the image detection apparatus 402 from the biological sample 404 is based on the focal point of the lens 420. For example, preferably the focal point is less than 5 cm for detecting images of a micro-array, corresponding to a light path that is less than about 6 cm. In one particular embodiment, distance from the lens 420 to the biological sample 404 is about 2 inches. Preferably, the closer the lens 420 can be positioned relative to the biological sample 404, the better, as such positioning provides for better light capture.

In more general terms, preferably, the light path between the biological sample and the detector pixels is in the range of 4 cm to 8 cm. One skilled in the art will recognize that as the object being imaged becomes larger, that the light path may be made larger with concurrent modification of the lens system.

Further, as the emission filter 450 is interchangeable with other filters for blocking different wavelengths and different wavelengths are used for the source light, multi-fluorescent imaging can be achieved. For example, one filter can be substituted for another during the imaging procedure to provide images of multiple colors that can combined into a single image for a particular biological sample.

The image detection apparatus 502 of FIG. 14 is substantially equivalent to that shown in FIG. 13 except that the excitation light is provided by a laser based source as opposed to LEDs to provide for higher resolution. As shown in FIG. 14, the excitation light is provided by one or more lasers 570, preferably a plurality of lasers, that provide illumination lines that are reflected by appropriately positioned corresponding mirrors 575. The reflected light from the mirrors 575 impinges on corresponding dichroic prisms 580 and is passed through corresponding diffusers 585 to provide diffused excitation light 590. For example, LED lasers having a power in the range of about 4 mW to 10 mW may be used to produce light in the wavelength of 570 nm and 660 nm corresponding to the Cy3 and Cy5 markers. Any number of lasers can be used as would be known to one skilled in the art.

In accordance with one embodiment of the present invention, a biological sample archiving method may be employed using an image detection apparatus as shown and described with reference to FIGS. 12–14. For example, each imaged biological sample (e.g., a DNA chip 14 as shown in FIG. 8A) may include a bar code 590 (as shown in FIG. 8A) associated therewith. As conventional bar code readers modified herein typically are configured with the necessary software for reading bar codes, the modified bar code reader can be employed in a bar code reading mode to associate a particular image, e.g., fluorescence image, with a particular imaged bar code. Such samples may then be archived using the read and stored bar codes associated with the corresponding fluorescence images.

Figure 15A:
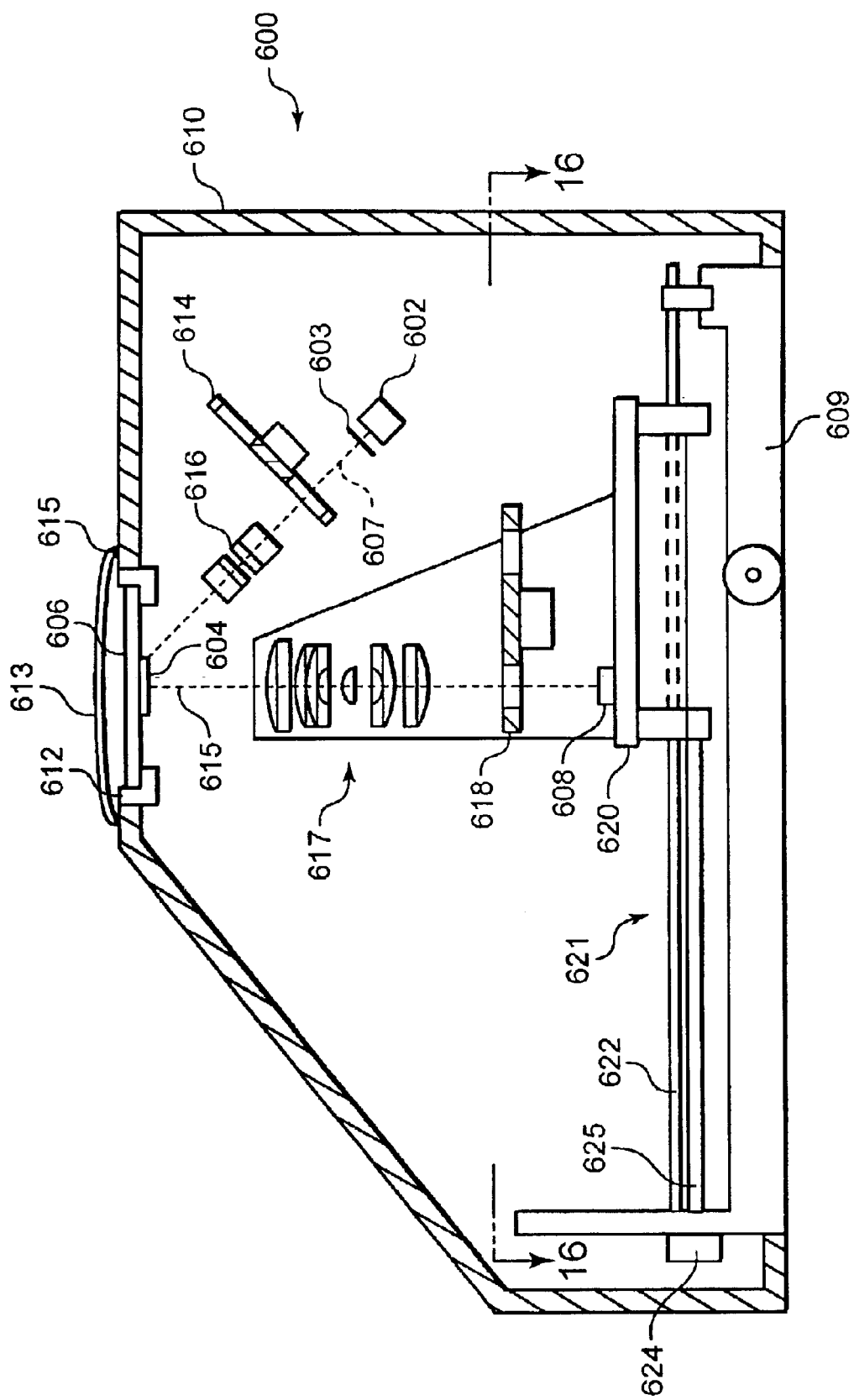
FIG. 15A illustrates another alternative embodiment of an image detection apparatus in side part-section view.
Figure 16:
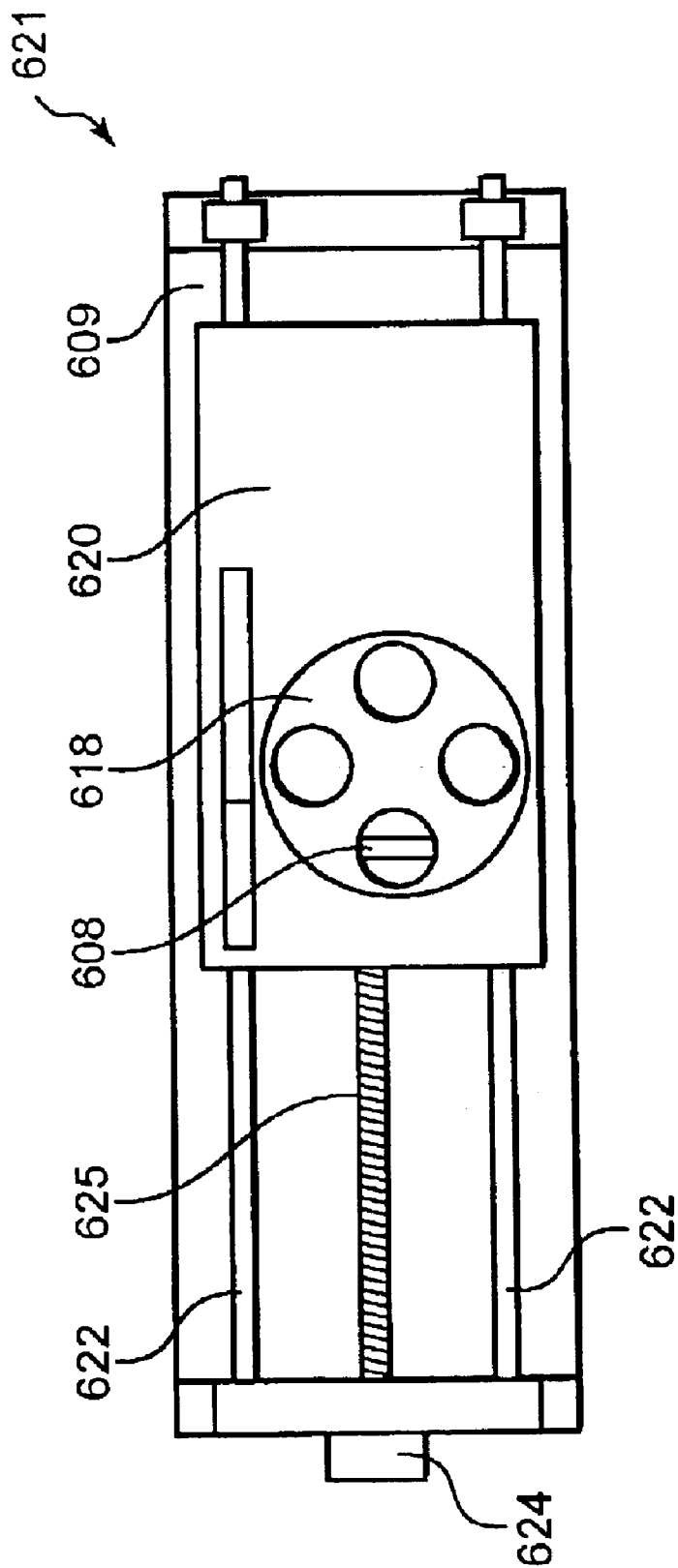
FIG. 16 shows a top view of the transport mechanism of the apparatus of FIG. 15A.

FIG. 15A illustrates another alternative embodiment of an image detection apparatus in side part-sectional view. For clarity, certain supporting structures have been omitted from the figure. In general, the system operates by impinging light on markers on a sample and causing them to generate light that may be scanned by a light detector. As shown, image detection apparatus 600 provides light from light source 602 to biological sample 604, and thereby causes light to be emitted from biological sample 604 onto light detector 608. In this embodiment, light detector 608 is a one-dimensional, linear light detector array, such as a linear charge coupled device (CCD) array (that is, a plurality of individual pixels, arranged in a line perpendicular to the page of FIG. 15A, as shown in FIG. 16). Light detector 608 may also be a multi-dimensional array that is smaller than the image projected from biological sample 604. A full two-dimensional image of biological sample 604 may be constructed by scanning light detector 608 across the light emitted from biological sample 604 so as to capture multiple images, which may then be combined to form the full, two-dimensional image.

The components of image detection apparatus 600 may be contained in a light-tight housing 610. In this manner, light may be provided to biological sample 604 without interference from the outside, ambient light. Likewise, various sub-housings may also be provided inside housing 610 to prevent light from one part of the apparatus from interfering with light from another part. Housing 610 may also contain electronic components and a power supply (not shown) for controlling and operating the other components. Preferably, the power supply is located to minimize thermal effects on biological sample 604 or on image detector 608.

Light is provided to biological sample 604 from light source 602. Light source 602 may, for example, produce ultraviolet or blue light that is intended to cause fluorescence or another detectable response from biological sample 604. Examples of suitable light sources are LED cluster arrays, tungsten filaments, and light lasers. As one example, three sets of LEDs may be used, chosen respectively for excitation of the CY3, CY5, and fluorescien fluorophores. The LEDs may have very high intensity (for example, in the range of tens of candela) and very small viewing angles. Suitable LEDs include the Fairchild Semiconductor MV8704 super bright orange LED or Luxeron Star LEDs in red/orange for CY5 excitation, the Fairchild Semiconductor MV8R03 super bright green LED or Luxeron Star in green for CY3 excitation, and the Fairchild Semiconductor MV8U03 super bright blue LED or Luxeron Star in blue for fluorescein excitation. The LEDs may be arranged in linear groups of LEDs, and may also use additional lenses, reflectors, or shields to increase intensity and approximate an "on axis" light source.

Source light from light source 602 follows a light path, indicated by dotted line 607, between light source 602 and biological sample 604. Beam expander 603 may be located in light path 607, and may expand the light directed at biological sample 604 so that the light provides adequate coverage of sample 604.

Filter 614 may also be located in light path 607, and may be used to remove particular wavelengths of light from the source light that impinges on biological sample 604 or to otherwise alter the character of the light. Filter 614 pre-filters the LED illumination and reduces cross talk between excitation light and emission light to and from biological sample 604. For example, for the LEDs specified above, for CY5 response, exciter filter HQ 620+/−60 nm, dichroic filter Q 660 nm long pass, and emitter filter HQ 700+/−75 nm are appropriate; for CY3 response, exciter filter HQ 535+/−50 nm, dichroic filter Q 565 nm long pass, and emitter filter HQ 610+/−75 nm are appropriate; and for GFP response, exciter filter HQ 470+/−40 nm, dichroic filter Q 495 nm long pass, and emitter filter HQ 525+/−50 nm are appropriate (all model numbers represent filters from Chroma Technologies). Alternative filters may be obtained from other manufacturers. Alternatively, filter 614 may be unnecessary if the fluorescence signal emitted from biological sample 604 has adequate amplitude relative to any source light reflected by biological sample 604.

Illumination lens assembly 616 may be provided in light path 607 to focus light from light source 602 in a line focus onto biological sample 604. Illumination lens assembly 616, in this embodiment, comprises a pair of toroidal collection lenses, identical in shape, having their curved surfaces facing each other. The lenses may be glass or plastic, for example, uncoated molded acrylic. A light trap (not pictured) may be provided behind substrate 606 to prevent reflection of light that passes around or through substrate 606.

Biological sample 604 is held in a position at which source light may impinge on at least a portion of it. Biological sample 604 may be mounted to a surface of a substrate 606, such as a DNA chip, which may be held in place in a holding apparatus, such as well 612. As shown in the figure, biological sample 604 is mounted to the lower surface of substrate 606. Biological sample 604 may comprise, for example, DNA or RNA material along with a label having a flourophore, chromophore, or other light emitting or absorbing moiety.

Well 612 may have a shape similar to that of substrate 606, and may be slightly larger than substrate 606 so that substrate 606 may fit snugly inside well 612. A spring-loaded mechanism (not pictured) or other similar mechanism may be provided to hold substrate 606 tightly, so that substrate 606 may be held in a registered position so as to ensure that source light will impinge on biological sample 604. In addition, well 612 may be provided with recesses (see FIG. 17A) on each side of substrate 606 to allow room for the fingers of an operator to set substrate 606 in place. A tray (not pictured) may also be provided under well 612 to prevent any material, such as pieces of a broken substrate, from entering housing 610. Well 612 may also be part of a movable platform, so that substrate 606 is loaded with the platform in a first position, and the platform is then moved into a second position to hold substrate 606 in a registered position relative to the other components of image detection apparatus 600. For example, a sliding platform may be pulled out of housing 610 for loading of substrates, and may be slid back into housing 610 for scanning. A movable light-tight cover 613 may also be provided over substrate 606 to prevent ambient light from interfering with the scanning process. Cover 613 may be locked in a closed position while a scan is occurring to prevent accidental interference with a scan.

Biological sample 604 may emit light as a result of its exposure to source light, such as by fluorescence or chemiluminescence. As an example, biological sample 604 may be a micro-array having fluorescent tagged nucleic acids thereon, where particular "dots" on the chip would then represent a characteristic of the sample at a particular location, as described above. The emitted light from biological sample 604 may travel along a light path from biological sample 604 to light detector 608, as indicated by dotted line 615. In addition, source light may be reflected off biological sample 604 and its surrounding structure.

Imaging lens assembly 617 may be positioned in light path 614 to collect and focus the image from the light emitted from biological sample 604 onto light detector 608. In general, the alignment and other tolerances for the imaging lens assembly are tighter than for the illumination lens assembly 616. In one embodiment, imaging lens assembly 617 has optical parameters as shown in the following table.

| | |
|---|---|
| Effective Focal Length (EFL) Range | 40.0–50.0 mm |
| Magnification Range | 0.8 x–1.25 x (nominal = 1.00 x) |
| Spectral Range | 500–700 nm |
| Numerical Aperture (NA) | Greater than 0.09 at 1:1 (working f/# = 5.5 or less) |
| Field of View (FOV) | 26 mm (+/−13 mm) circular |
| Distortion | <0.5% |
| Field Curvature | <0.15 mm total |
| Resolution | Essentially diffraction limited across whole FOV (blur spot = 9 $\mu$m dia.) |
| Modulation Transfer Function (MTF) | >200 cy/mm across whole FOV |
| Encircled Energy | >70% for 9 $\mu$m circle |
| Transmission | >80% |
| Overall Length (vertex to vertex) | <50 mm |
| Object-Image Distance | 150–200 mm range |

Imaging lens assembly 617 focuses emitted light representative of biological sample 604 into a line focus that impinges on linear light detector 608. To the extent there is nonuniformity along the length of the line focus that cannot be removed from the system, such nonuniformity may be compensated for electronically. For example, the nonuniformity may be measured at the factory and adjustments may be made to the system's image processing software to boost dark areas and darken light areas.

Substrate 606 may be placed in a predetermined, repeatable position, so that the optical focus through imaging lens assembly 617 may be preset. However, a setscrew (not pictured) may be provided to allow for adjustment of the optical focus. Alternatively, the focus may be adjusted by other means, including by automatic focus, though the disclosed design is generally capable of operating well without automatic focus.

Filter 618, located in light path 615, eliminates background and scattered illumination and thereby helps to increase signal-to-noise ratio of the apparatus. As shown in FIG. 16, filter 618 may comprise a rotating filter wheel having one or more filter elements, so that a given filter element may be positioned interchangeably along light path 614, depending on the characteristics of a particular sample or the light source.

Referring again to FIG. 15A, light is directed to light detector 608, which may be a CCD mounted in a DIP-style package, and in one embodiment is capable of imaging a minimum spot size of 40 $\mu$m at a minimum distance between spot edges of 27 $\mu$m. Using the Johnson criteria to resolve minimum features, the detector pixels may be 9 $\mu$m with a pitch of 9 $\mu$m. The detector should also be adequately sensitive to detect light from a sample, depending on the expected extinction coefficient of fluorophores in the sample, the quantum yield of the fluorophores, expected light losses, quantum efficiency of the detectors, gain control, optical path, and other relevant factors. Given an expected gene chip size of approximately 25.4 mm×76.2 mm, appropriate detectors include the NEC UPD3594D, the Loral CCD182D, and the Loral CCD181EDC. For example, the latter detector provides 2592 horizontal pixels, a 10 $\mu$m pixel dimension, 18.4 V/x*s sensitivity, and a dynamic range of 7500. In addition, a full-color, multi-layer image sensor, such as that made by Foveon, Inc. (Santa Clara, Calif.), could also be used.

Figure 15B:
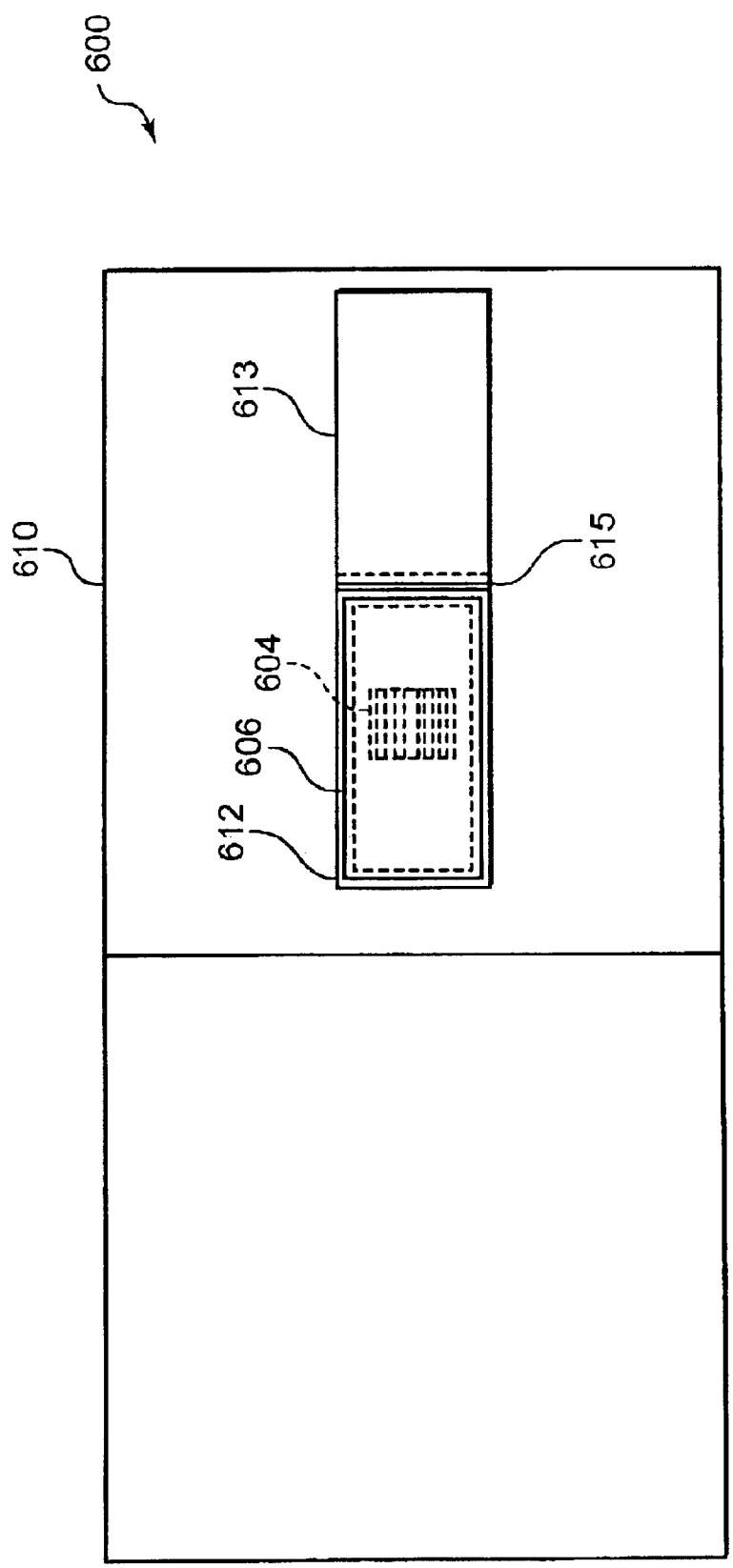
FIG. 15B illustrates the embodiment of FIG. 15A in top view.

FIG. 15B shows the apparatus of FIG. 15A in top view. Movable light-tight cover 613 is shown in an open position, to allow for loading and unloading. Substrate 606, which has biological sample 604 on its lower surface, is shown held in position by well 612. Well 612 defines an opening in housing 610 so that biological sample 604 may be viewed from inside housing 610. Cover 613 may be closed over the top of substrate 606 to prevent ambient light from entering housing 610 during the operation of the apparatus. For example, cover 613 may be rotated about hinge 615 and flipped back until well 612 can be accessed easily. Alternatively, substrate 606 may be placed in a tray (not shown) that may slide into or out of housing 610.

FIG. 16 shows a top view of the transport mechanism 621 of the apparatus of FIGS. 15A–B. Light detector 608, lens assembly 616, and filter 618 may be mounted to carriage 620, which is part of transport mechanism 621. The figure shows the positioning of the linear light detector array 608 of the particular embodiment relative to the other components of the apparatus. Transport mechanism 621 may allow light detector 608 to move so as to cause light detector 608 to scan across biological sample 604. In particular, carriage 620 rides laterally on rails 622 that are mounted to transport base 609 under the control of stepper motor 624. Rotary motion of stepper motor 624 is translated into linear translational motion of carriage 620 by lead screw 625 attached at one end to stepper motor 624 and at the other to carriage 620. Stepper motor 624 may have, for example, fifteen steps per revolution so that carriage 620 is moved across three inches in 9 $\mu$m increments while acquiring a scanned image. The 9 $\mu$m resolution may be achieved, for example, by half-stepping the motor 624. A flag (not pictured) on carriage 620 may extend across the beam of a photointerupter, such as a Sharp GP1A75E, to indicate when carriage 620 is in its "home" position.

As mentioned above, light passes through filter 618 to light detector array 608. As shown, filter 618 may comprise a rotating filter wheel containing one or more filter elements so that a given filter element may be positioned interchangeably along the light path, depending on the characteristics of a particular sample. Additionally, with reference to FIG. 15A, filter 614 may also comprise a rotating filter wheel containing one or more filter elements.

As carriage 620 is scanned, light detector array 608 may be controlled to retrieve a plurality of images at spaced positions, as part of a continuous or stepped scanning motion. These images will each be a "slice" of the entire image representative of biological sample 604 and may be output individually from light detector array 608 for later combination into a single larger image. The total scanned area may be larger than the area of interest to ensure that the entire biological sample is scanned. In addition, adjustments may be made to the carriage to correct for any misalignment. Alternatively, multiple linear arrays or a two-dimensional linear array may be provided to increase the space between points at which an image is captured and thereby decrease the number of required capture events.

Referring to FIGS. 15A–B and 16, in operation, an operator opens cover 613 and places substrate 606 containing biological sample 604 upside down into well 612. The operator then closes cover 613, and in one embodiment, well 612 slides from its loading position into imaging position, for example, by being pushed inward by the operator, and holds substrate 606 in a registered location relative to optical carriage 620. The carriage 620 may be kept in a "home" position (at the left in FIGS. 15A and 16) away from substrate 606 during loading, and may move under substrate 606 once substrate 606 is set into position. The operator may then initiate a scan. Carriage 620 will be caused to move, for example, from left to right in FIGS. 15A and 16, so as to pass light detector array 608 through the light emitted from biological sample 606. At defined points along the scan, light detector array 608 captures an image of the emitted light, and passes the image to processing circuitry (not pictured, but shown in later figures). When the scan is complete, the operator may open cover 613 and remove substrate 606.

In the pictured embodiment, no mirrors, such as fold mirrors, are used to redirect either the source light path 607 or the emitted light path 615. Advantageously, this helps ensure that maximum light intensity is delivered to light detector 608. For example, fold mirrors typically reflect only approximately 88% of visible light. However, mirrors could be used to redirect light paths 607, 615, and could also be rotated so as to scan light path 615 across light detector array 608, even as light detector 608 and biological sample 604 are kept stationary.

By scanning light detector 608 across the light that is emitted from sample 604, this embodiment can provide several advantages. For example, a high-resolution, scanned linear (one-dimensional) light detector array that acquires multiple images of portions of a sample may be less expensive than a high-resolution, two-dimensional array that "stares" at the sample to acquire an image in a single exposure. In addition, because the number of pixels in a given array is limited, a two-dimensional array sized to capture an entire image at once may have to sacrifice resolution in one dimension to provide adequate coverage in a second dimension. A scanned linear array may, at the same time, acquire an image more quickly than a system that acquires an image one pixel at a time, for example, by rastering a laser across a sample. In addition, linear light detector arrays are commercially available at adequate resolutions, and a system may be constructed largely from off-the-shelf components similar to those used in commercially available scanners that are designed to scan images from objects such as photographic negatives. One example of such a commercially available scanner is the Nikon CoolScan IV Film Scanner.

Figure 17A:
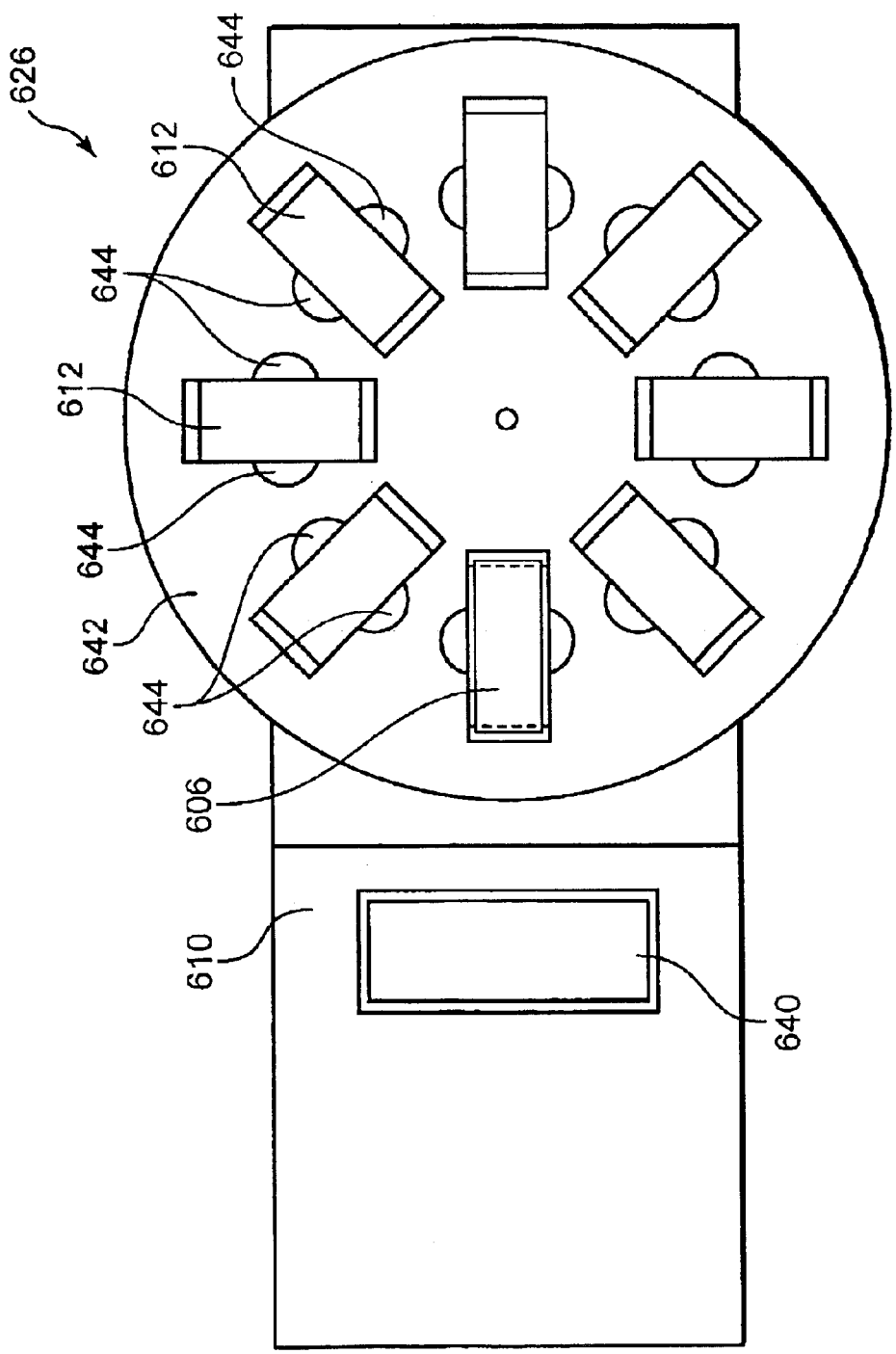
FIGS. 17A and 17B show, respectively, a top and a side exterior view of an image detecting apparatus having an added multi-sample mechanism.
Figure 17B:
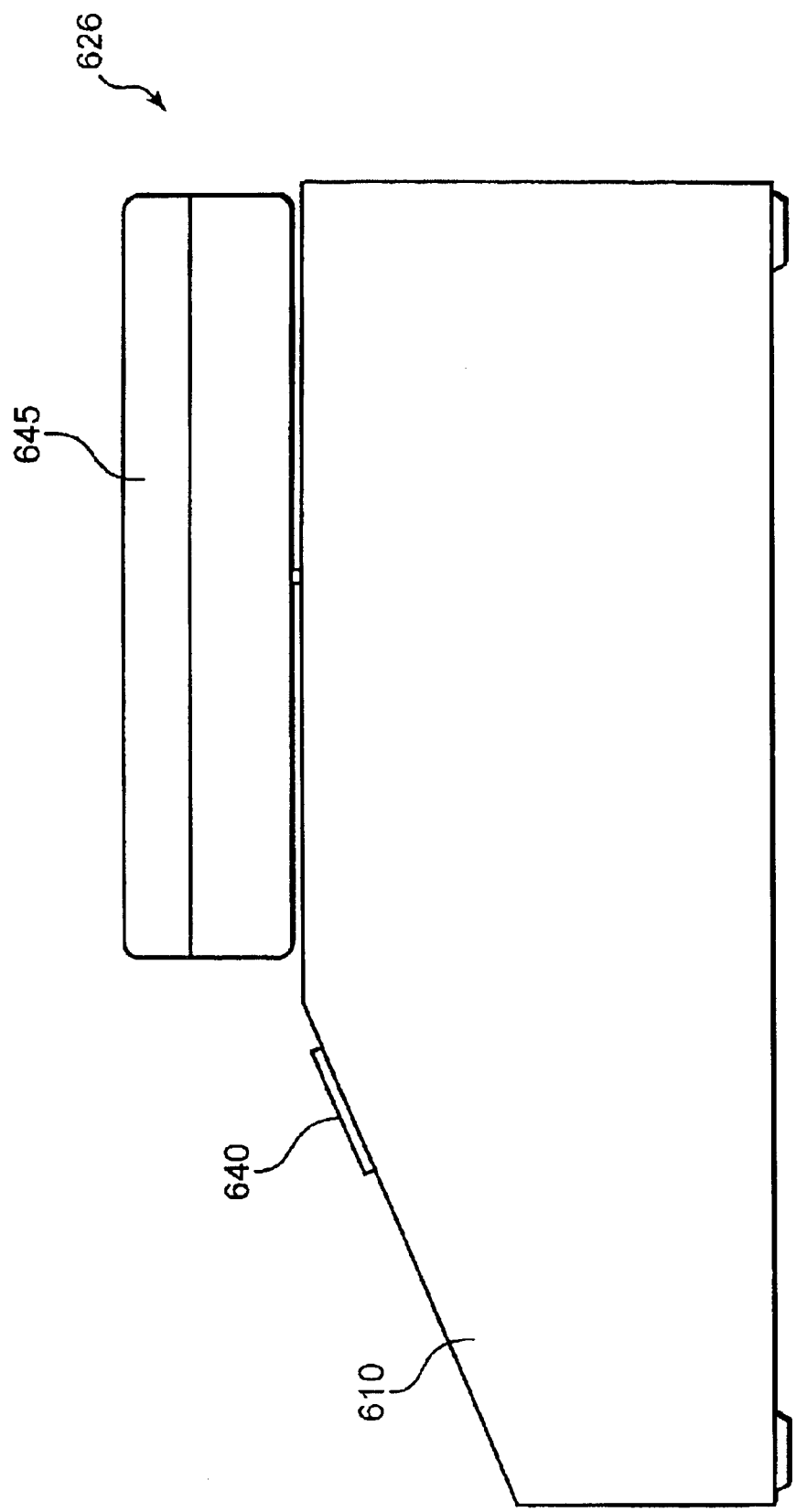

FIGS. 17A and 17B show top and side exterior views, respectively, of another embodiment of an image detection apparatus 626, similar to that shown in FIGS. 15A–B, but having an added multi-sample mechanism. Housing 610 may include panel 640 on its surface, which may comprise an LCD display, a touch sensitive display, and/or controls such as buttons. Panel 640 may provide a visual indication of the operation of image detection apparatus 626, and may also contain controls for turning apparatus 626 on or off, or for initiating a scan. A rotating sample carousel 642 is mounted on top of housing 610 and is capable of holding a plurality of substrates 606 in wells 612. Recesses 644 in opposing sides of each well allow an operator to place or remove samples easily. In addition, as shown in FIG. 17B, a light-tight cover 646 may be provided on carousel 642 during scanning.

In operation, an operator may open cover 646 and place samples into one or more wells. The operator may then close cover 646, and the samples may be scanned in turn automatically by rotating each sample into scanning position. Other arrangements for scanning multiple samples will be apparent to a skilled artisan. For example, substrates 606 could be placed front-to-back in a circular ferris-wheel arrangement, so as to fit more slides into the mechanism, and each slide could be pulled out of the circle for scanning.

Figure 18A:
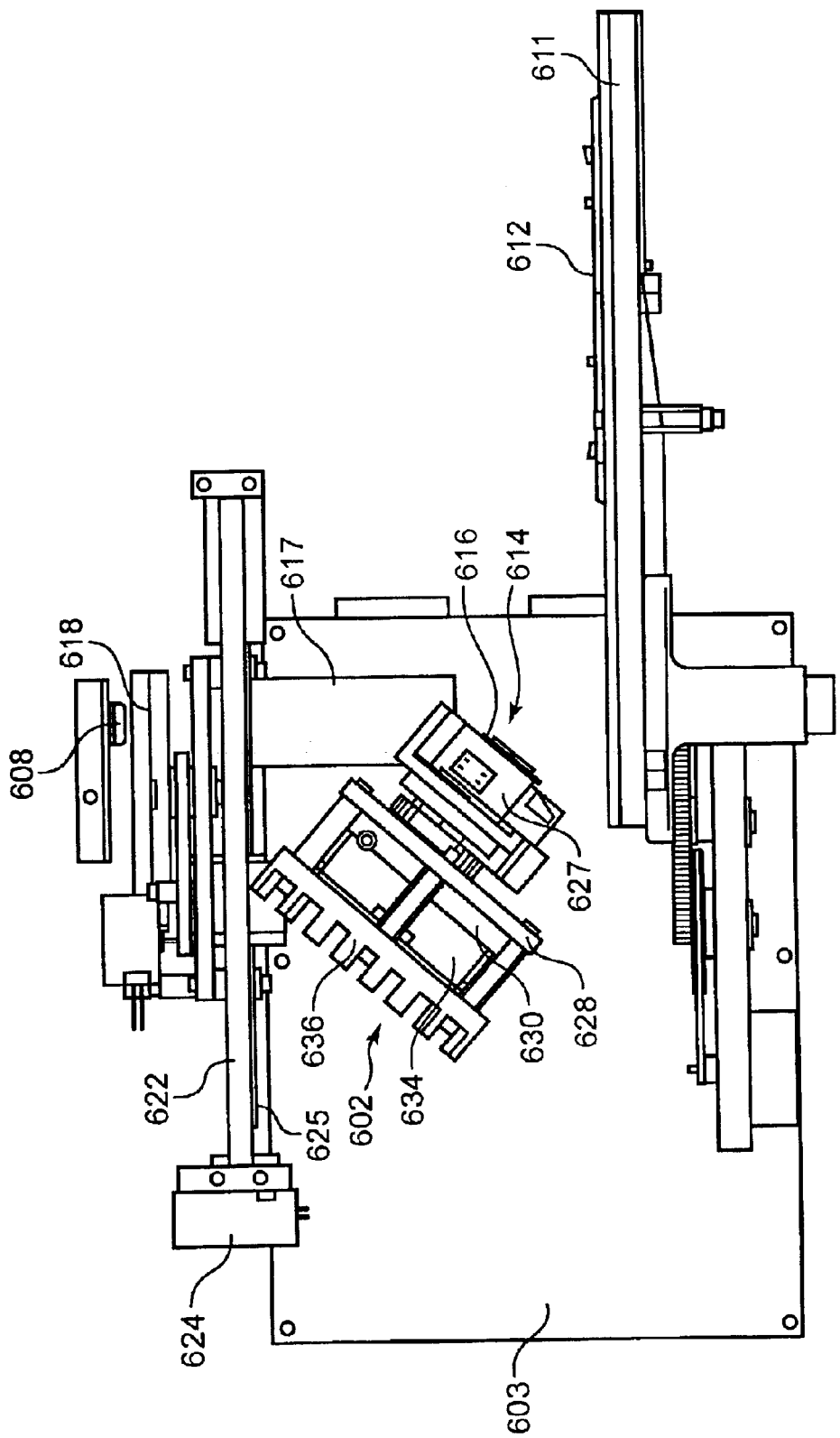
FIGS. 18A–18C show another embodiment of an image detection apparatus.
Figure 18B:
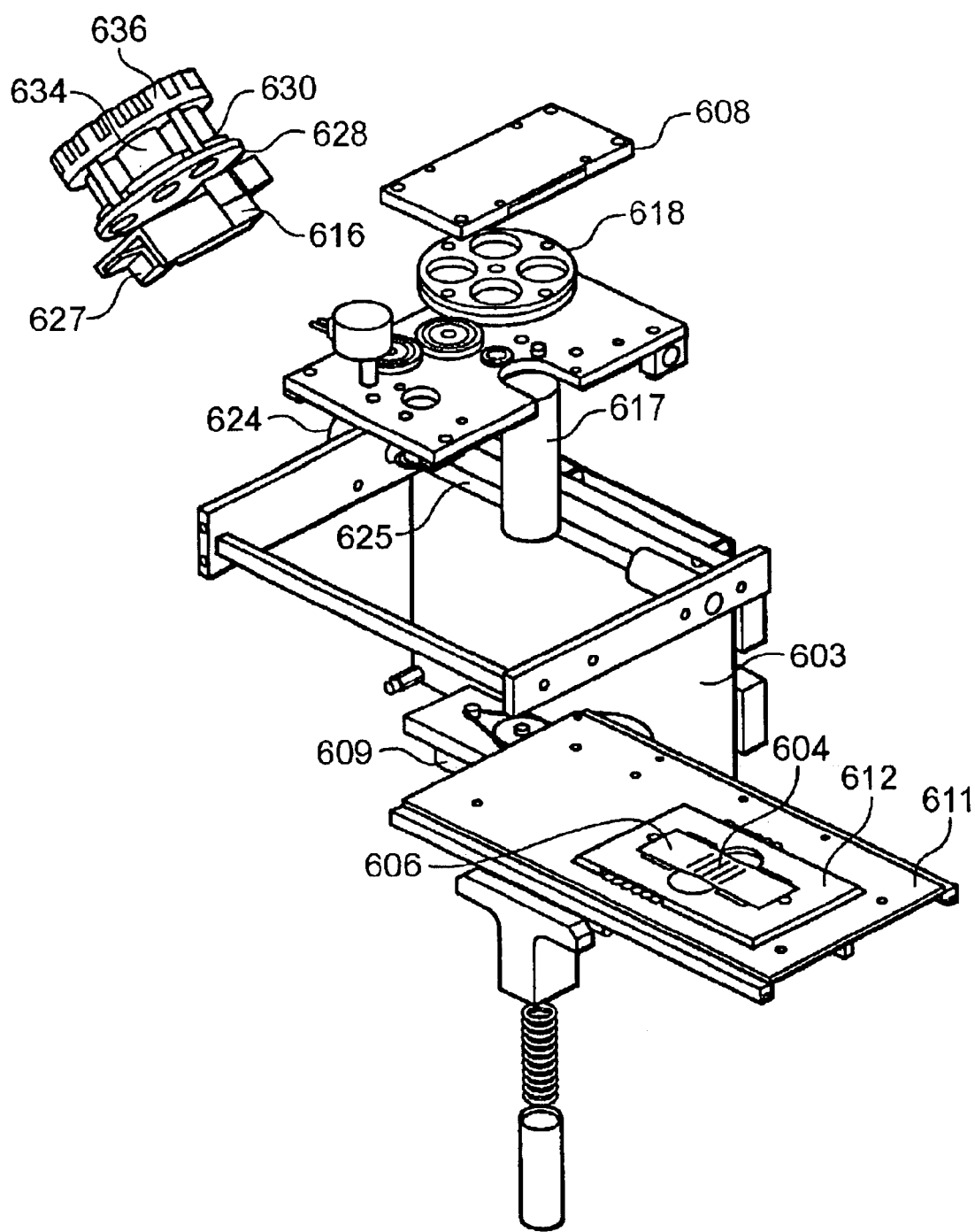
Figure 18C:
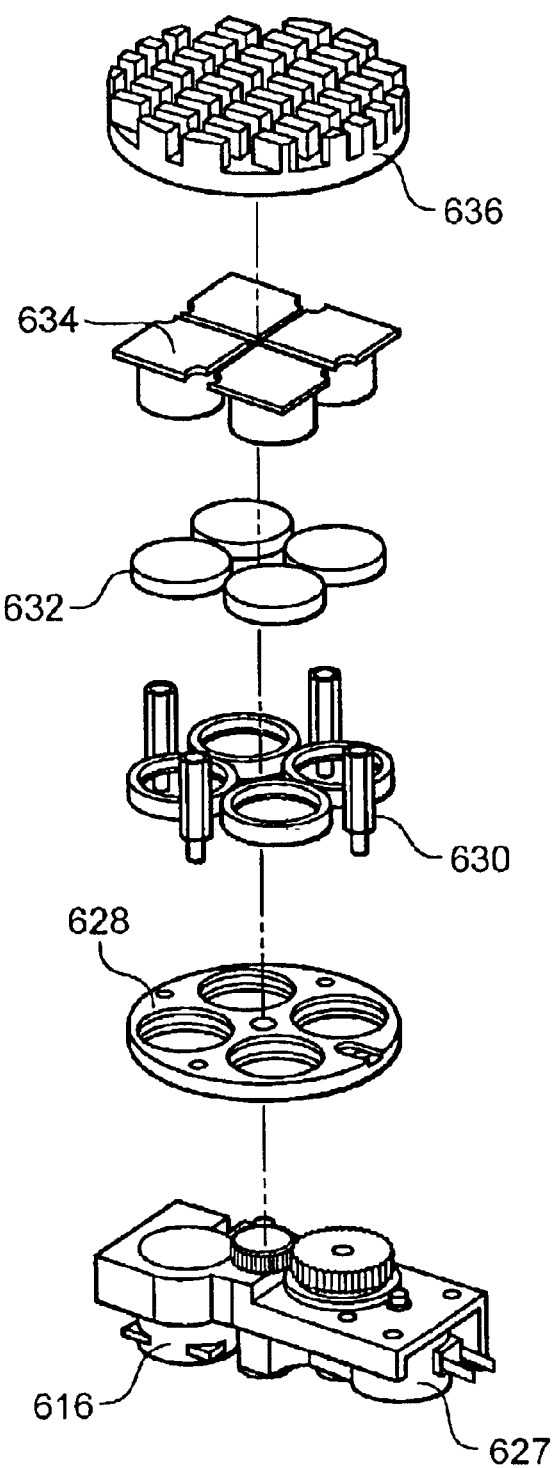

FIGS. 18A, 18B, and 18C show the components of an alternative embodiment of on an image detection apparatus. FIG. 18A shows the components in side view, while FIGS. 18B and 18C show the components in exploded perspective view. In general, the apparatus is similar to that depicted in FIGS. 15A and 15B, but inverts the relationship of the biological sample to the light source and the image sensor.

As pictured, light source 602 provides light to to a biological sample 604 through filter 614. Light source 602 may contain a plurality of LEDs that may be attached to a printed circuit board and backed by a heat sink, and that may receive pulsed DC power to created illumination. Light from the LEDs may pass through lenses 632 held in lens holders 634, 630. The light may pass through filter 614, which may contain a plurality of filters in filter wheel 628, which may be rotated under the control of filter motor 627. Light may then pass out of the assembly through illumination lens assembly 616, which may be configured to focus the light substantially along a line on biological sample 604. As discussed above, illumination lens assembly may comprise a pair of toroidal collection lenses, identical in shape, having their curved surfaces facing each other.

In this embodiment, biological sample 604 is shown mounted on a substrate 606 that is held in position in a well 612 that is mounted on a sliding tray 611. The tray 611 may be ejected from the housing (not shown) under the power of sample positioning motor 631, and may be subsequently withdrawn back into the housing, for example, when a new sample is placed on the tray. In general, tray 611 is adapted to hold substrate 606 in a registered position during the scanning of biological sample 604.

Light detector 608 is positioned to capture the light emitted from biological sample 604. Light detector 608 may be mounted as part of an assembly that slides on rails 622 under the power and control of stepper motor 624 and lead screw 625. In addition, filter 618 may be optinally provided, for example, to remove light in wavelengths that are different from the wavelengths of the light that is expected to be emitted from biological sample 604. In addition, imaging lens assembly 617 may also be mounted so as to move along with light detector 608 and filter 618. As such, the entire image collection assembly can be scanned across the image of light that is emitted from biological sample 604, and may thereby capture a full image of the sample.

Figure 19:
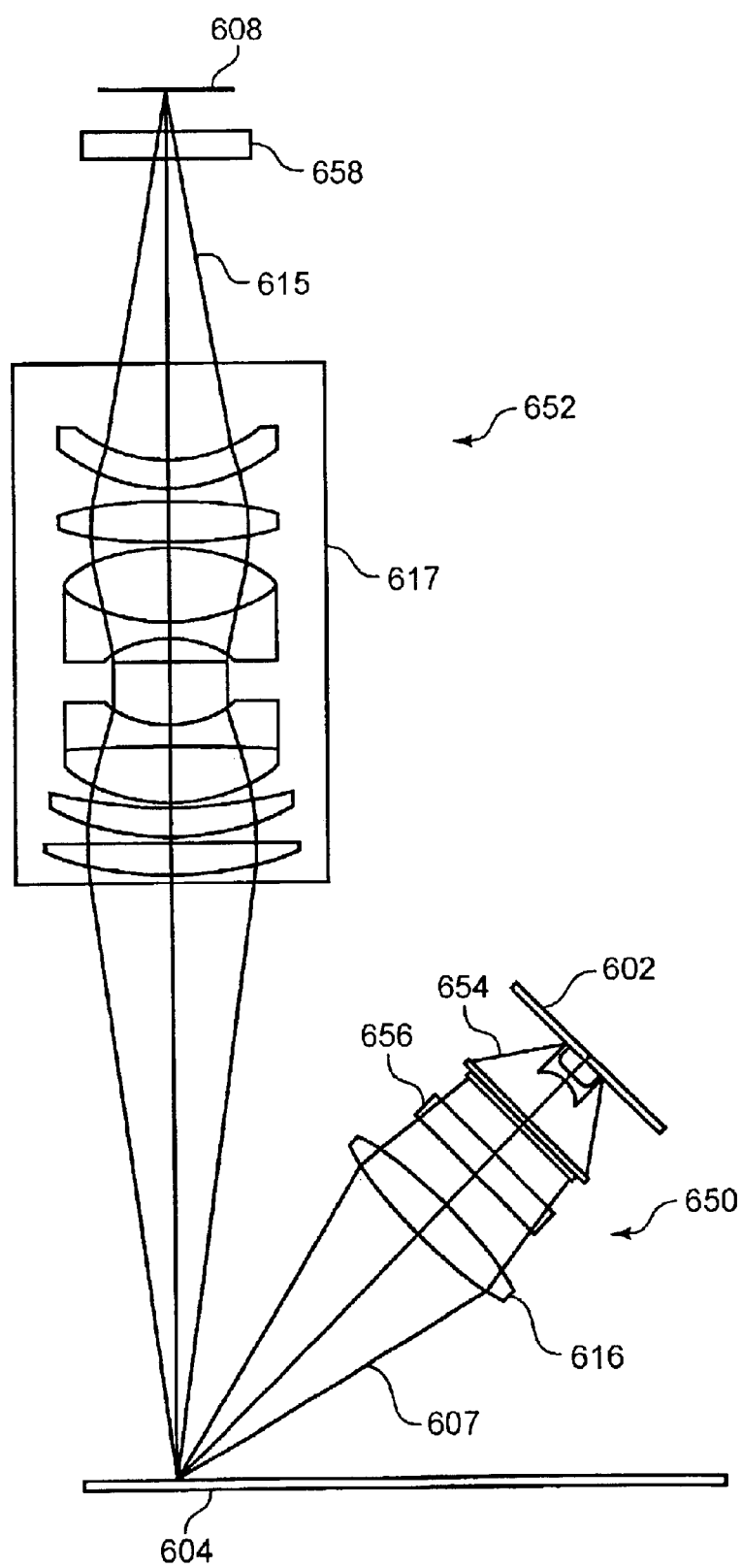
FIG. 19 shows schematically an optical arrangement that may be used with the apparatuses of FIGS. 15–18.

FIG. 19 shows, in schematic form, an optical system suitable for use in the the apparatuses of FIGS. 15–18. The optical system may include two main assemblies: an illumination optics assembly 650 and a viewing optics assembly 652. The illumination optics assembly 650 delivers filtered light from a light source 602 onto a biological sample 604, while the viewing optics assembly 652 uses the light emitted from the biological sample to produce a focused image of at least part of the sample onto a light detector 608, such as a CCD.

The illumination optics include light source 602, which may be one or more LEDs emitting light of a particular wavelength range (or having a particular frequency range), or other appropriate high-brightness source. The LEDs may be mounted to a printed circuit (PC) board, and light from light source 602 may pass through two stages. In the first stage, a collimation optics light pipe 654 may collect the light. The light pipe 654 may then direct the collimated light through excitation filter 656 to the second stage— illumination lens assembly 616. Excitation filter 656 may be provided in the light path to provide selective transmission of source light. Excitation filter 656 may be a thin-film dielectric stack structure. For example, excitation filter 656 may serve as a long-pass wavelength selector with a very steep transition region (from blockage to transmission), which may be selected so that the cut-on region is above the expected flourescence or other emitted wavelength of light from sample 608. Illumination lens assembly 616 may comprise, for example, an anamorphic toroidal or toroidal-like lens that is configured to focus the light into a line with good uniformity along the length of the line. For example, the line may be about 1 mm wide by 22 mm long, with a uniformity along the length of the line within +/−10% of the peak illumination level.

Viewing optics assembly 652 images emitted light from sample 612 onto light detector 608. For example, sample 612 may be comprised of fluorescing fluorophores on the surface of a microscope slide whose emitted light is directed toward light detector 608. The illustrated viewing optics assembly 617 comprises a six-element double-Gauss lens system that operates at f/3.6 in image space so as to produce favorable energy capture characteristics. For example, the objective lens may have an NA of 0.133 and work at a magnification of 0.75× (sample to detector) to produce an f/2.8 imaging cone at detector 608. The lens may achieve low crosstalk (approx <5%) between fluorescing patches of sample 612 that are spearated by 0.025 mm or more, and may do so over the waveband from 450 nm to 650 nm.

Emission filter 658 may also be provided in the emitted light path ahead of detector 608. Emission filter 658 may be selected as the complement of excitation filter 656. As such, it may be a cut-off filter that allows the desired emitted light from sample 612 to be transmitted to detector 608, while effectively blocking the remaining spectrum of light, such as light from light source 602 or ambient light from the scanner or the surrounding room.

Concentrating the light along a single line that is parallel to the direction of detector 608 helps to maximize the amount of the generated light that reaches detector 608. In addition, energy from a "point source" may be directed to each pixel of light detector 608. In this manner, viewing optics assembly 652 can efficiently capture and reimage the emitted light. Advantangeously, the described optical system may provide high light levels at light detector 608 without the need to use expensive optical components.

In addition, illumination optics assembly 650 is positioned off axis and illuminates sample 612 from the same side as viewing optics assembly 652. This arrangement allows a high level of illuminating light to pass through the substrate on which sample 612 is mounted (if the substrate is translucent) and captured in a light trap, so that the scanner can produce a high signal-to-noise (SNR) ratio at light detector 608. As a result, the scanner may produce a good gray-scale range in the captured image data. Furthermore, light baffles (not pictured) may block additional light and thereby enhance the SNR characteristics of the scanner.

Advantageously, this finite-conjugate optical arrangement provides a system that can image a sample that has considerable optical depth in a fixed focus manner. For example, fixed focus depths of field in the range of +/−50 microns or greater may be realized, even though only a particular level of a sample may be imaged. In addition, the arrangement can operate relatively efficiently, in part because the imaging need not occur through a pinhole mechanism as with other imaging arrangements. Also, the time to scan a sample may be reduced from other scanning approaches, and the system may be operated using either opaque or transparent substrates in particular embodiments. Moreover, the arrangement provides a relatively inexpensive system that is well-suited to the task of imaging biological samples. For example, images may be created in some embodiments by holding the light source and the substrate steady, and moving the image detector in a single axis.

Figure 20:
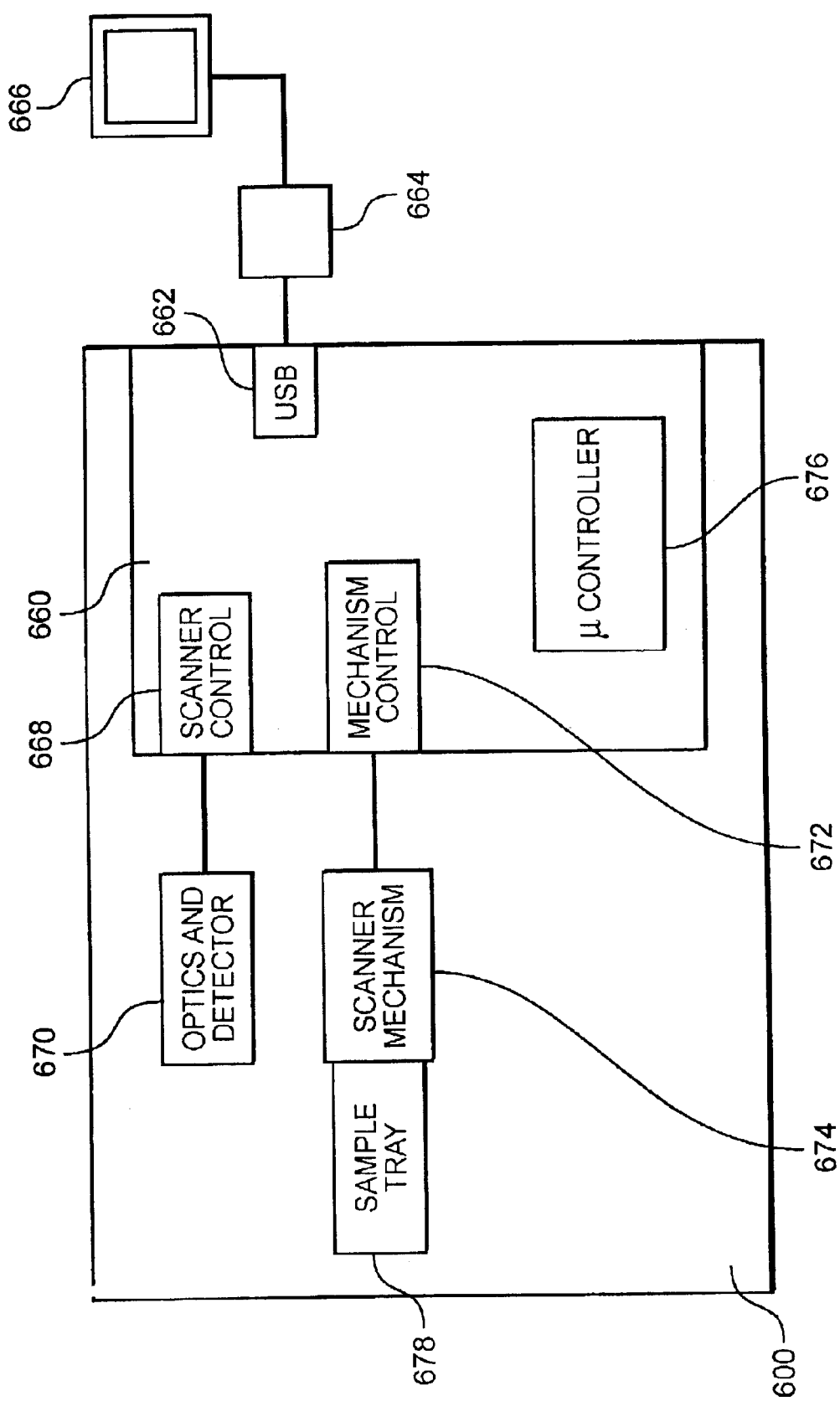
FIG. 20 is a block diagram showing the control mechanisms for an image detection apparatus.

FIG. 20 is a block diagram showing the control mechanisms for an image detection apparatus, such as that shown in FIGS. 15–16. Imaging components are located inside image detection apparatus 600, and are connected to an external computer 664 having a monitor 666 through a communication port, such as Universal Serial Bus (USB) port 662 mounted on control board 660. A processor, such as a microcontroller 676, may also be mounted on control board 660, and may provide commands for the operation of apparatus 600 and process image data acquired by apparatus 600. Control board 660 also contains scanner control 668 and mechanism control 672. Scanner control 668 manages the operation of the optics and detector in apparatus 600. For example, scanner control 668 may influence the energizing of LEDs to light a sample, and may control the position and focusing of optics, the use of filters, and the timing of image acquisition by the image detector. Mechanism control 672 manages the motion of whatever mechanism is used to perform the scanning. For example, mechanism control 672 may control a stepper motor that moves the image detector. Scanner control 668 and mechanism control 672 may cooperate so that the image detector acquires images at appropriate positions so that a complete image of the entire sample may be constructed from the plurality of acquired images.

Figure 21:
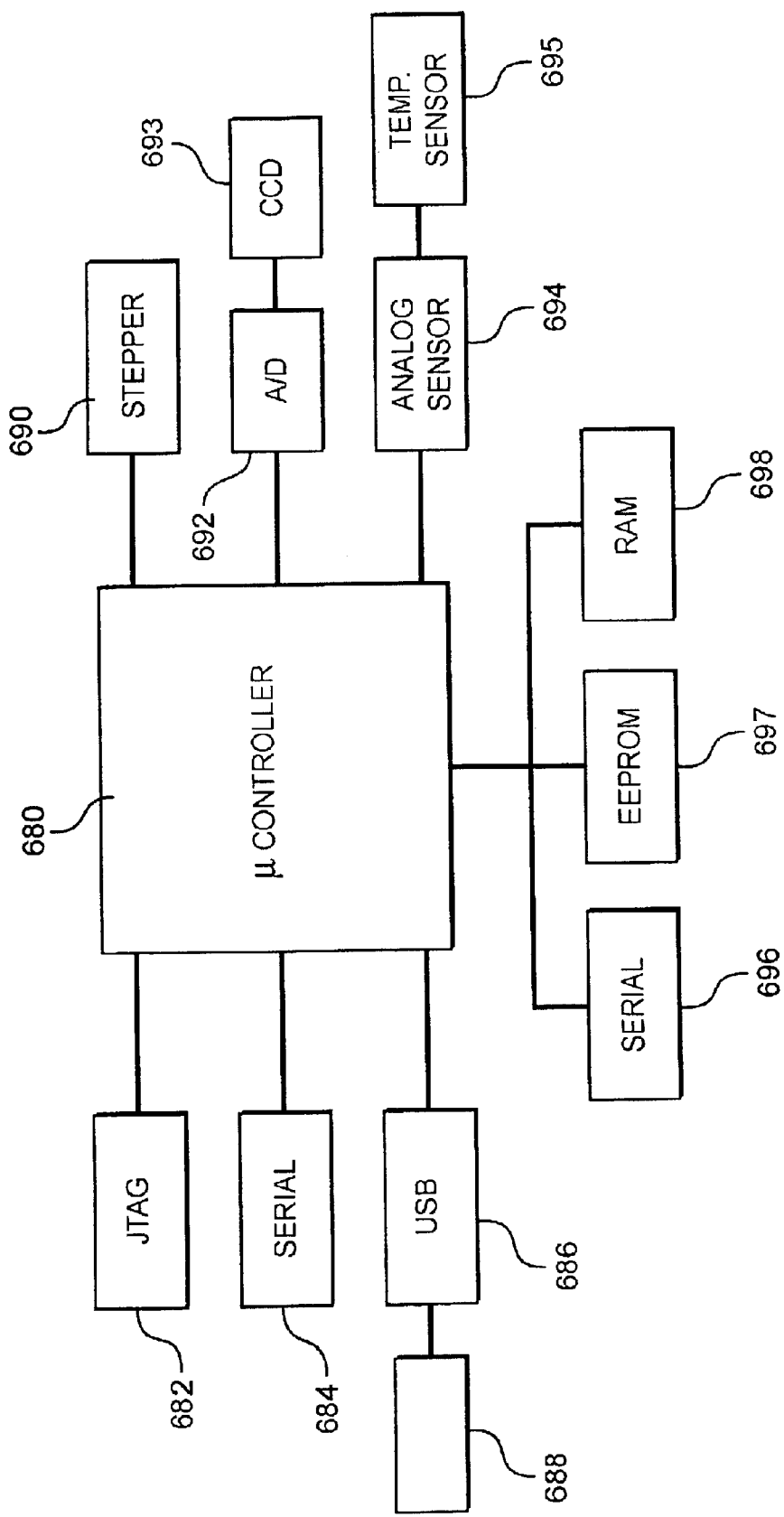
FIG. 21 is a block diagram of the control electronics in an image detecting apparatus.

FIG. 21 is a block diagram of the control electronics in apparatus 600, showing conceptually how the processor of FIG. 19 cooperates with other electronic components. The processor, in the form of microcontroller 680, serves as the centerpiece of the controls. Microcontroller 680 may include internal RAM and ROM memory, registers, timers, communication interfaces, and A/D or D/A converters. For example, microcontroller 680 may be a 16-bit Hitachi H8S or a 32-bit Hitachi SH3 7727. Analog-to-digital (A/D) converter 692 receives analog signals from CCD 693 and converts them into digital form to be sent to microcontroller 680. To resolve an accurate image, converter 692, in one embodiment, has twelve bits of resolution, and more preferably has sixteen or more bits of resolution. In addition, converter 692 also may have low integrated nonlinearity error (INL), high sampling rate, low signal-to-noise ratio, and low offset and gain errors. Examples of such converters include the Analog Devices AD7664, the Linear Tech LTC1604 and LTC1418, and the Maxim MAX1133. The Analog Devices converter, for example, has sixteen-bit resolution, 90 dB SNR, a DNL of +2.5 LSB, and a sampling speed of 575 kSPS. In operation, image slices may be received by CCD to be sent to a computer, as shown in FIG. 19.

Referring again to FIG. 20, microcontroller 680 may also receive data from temperature sensor 695 through analog sensor 694. Using this data, for example, microcontroller 680, or a computer to which apparatus 600 is connected, may make adjustments to the data to compensate for temperature effects. Boundary-scan interface 682, which may operate in accordance with IEEE 1149.1 (JTAG), may also be provided to support production testing and debugging of the other components used with image detection apparatus 600.

Microcontroller 680 may also control the scanning motion of the apparatus. For example, microcontroller 680 may provide output to stepper 690 to control the movement of the image detector or to a serial port 684.

Communication between microcontroller 680 and other devices outside the image detection apparatus (such as computer 664 pictured in FIG. 19) may occur though USB port 688, managed by USB controller 686. Image data may be transmitted from microcontroller 680 to USB controller 686 using a sixteen-bit interface, for example. USB controller 686 may be, for example, a stand-alone controller such as Cypress Semiconductor EZ-USB FX. Where image reconstruction is handled wholly or largely by the computer to which the image detection apparatus is connected (e.g., computer 664 in FIG. 19), the microcontroller 680 may be responsible only for image acquisition, and thus need not be as powerful as it otherwise would.

A number of embodiments of the invention have been described. Nevertheless, it will be understood that various modifications may be made without departing from the spirit and scope of the invention. For example, different methods of, and structure for, scanning an image detector across an image representative of a sample may be employed. In addition, various electronic circuitry configurations and means of processing, analyzing, and aggregating image data may be employed, since the system is intended to be easily adaptable to various analysis tools, including many off-the-shelf tools. Accordingly, other embodiments are within the scope of the following claims.

What is claimed is:

1. An image detection apparatus for use with a biological sample, the apparatus comprising:
    a light source that provides source light along a source light path;
    a holding apparatus to hold a substrate, on which a biological sample is mounted, in a position such that at least a portion of the source light impinges on at least a portion of the biological sample and causes light emission representative of the biological sample to be produced in the form of emitted light along an emitted light path;
    a light detector array comprising a plurality of detector pixels that is positioned in at least a portion of the emitted light path such that the array senses emitted light from the biological sample; and
    a transport mechanism adapted to translate the light detector array to allow the capture of an image of at least a portion of the biological sample as a plurality of sub-images.

2. The image detection apparatus of claim 1, wherein the light source comprises one or more light emitting diodes or laser diodes.

3. The image detection apparatus of claim 2, wherein the emitted light from a single micro-array address is directed to substantially one detector pixel.

4. The image detection apparatus of claim 1, wherein the biological sample is in the form of a micro-array comprising one or more sequences of nucleic acids immobilized to a substrate, each sequence immobilized at a particular micro-array address, wherein the nucleic acid sequences are positioned such that emitted light from a micro-array address is substantially directed onto at least one detector pixel of the light detector array.

5. The image detection apparatus of claim 1, wherein the substrate comprises an opaque material.

6. The image detection apparatus of claim 1, wherein the emitted light path does not pass through any part of the substrate.

7. An image detection system for use with one or more biological samples, the system comprising:
    a light source that provides source light along a source light path;
    a holding apparatus adapted to hold a substrate supporting a biological sample in at least a portion of the source light path such that the source light impinges on at least a portion of the biological sample, and produces emitted light representative of the biological sample along an emitted light path, wherein the source light path and the emitted light path are both on a first side of the substrate, and
    a light detector positioned in at least a portion of the emitted light path, and scannable across an image that is representative of the biological sample.

8. The image detection system of claim 7, wherein the light source comprises a plurality of light emitting diodes or laser diodes.

9. The image detection system of claim 8, wherein the plurality of light emitting diodes comprise a first group of one or more diodes that emit light at a first wavelength range, and a second group of one or more diodes that emit light at a second wavelength range that is substantially different from the first wavelength range.

10. The image detection system of claim 7, further comprising a source light filter positioned in the source light path to reduce interference between the source light and the emitted light.

11. The image detection system of claim 7, further comprising an illumination optics assembly positioned in the source light path, and having a light pipe and a toroidal or semi-toroidal focusing lens.

12. The image detection system of claim 11, wherein the illumination optics assembly comprises an excitation filter.

13. The image detection apparatus of claim 7, further comprising a viewing optics assembly positioned in the emitted light path for focusing the emitted light on the light detector.

14. The image detection apparatus of claim 13, further comprising a fixed focus imaging system.

15. The image detection apparatus of claim 14, wherein the apparatus has a depth of field greater than about 50 microns.

16. The image detection apparatus of claim 13, further comprising an emission filter positioned in the emitted light path between the viewing optics assembly and the detector.

17. The image detection system of claim 7, wherein the substrate has a first surface and a second surface opposing the first surface, and the biological sample is in the form of a micro-array comprising one or more sequences of nucleic acids immobilized to the first surface of the substrate, each sequence immobilized at a particular micro-array address, wherein the nucleic acid sequences are positioned on the micro-array such that light emitted from one micro-array address is substantially directed onto one detector pixel of the light detector.

18. The image detection system of claim 17, wherein the biological sample comprises a probe and a light emitting or light absorbing label.

19. The image detection system of claim 17, wherein the light from a single micro-array address is directed to substantially one detector pixel.

20. The image detection system of claim 7, wherein the emitted light comprises light of fluorescence from the biological sample.

21. The image detection system of claim 7, further comprising a lens assembly positioned in the emitted light path to focus the emitted light on the light detector.

22. The image detection system of claim 7, wherein the light detector comprises a linear array that further comprises a plurality of detector pixels.

23. The image detection system of claim 22, wherein the light detector comprises a charge coupled device (CCD).

24. The image detection system of claim 7, wherein the light representative of the biological sample comprises light provided by at least one of chemi-luminescence, fluorescence, chemi-fluorescence, photon excitation, phosphorescence, adsorption, and a quenching thereof.

25. The image detection apparatus of claim 7, wherein the apparatus has a depth of field greater than about 30 microns.

26. The image detection apparatus of claim 25, wherein the apparatus has a depth of field greater than about 50 microns 27. A method for detecting an image relating to a biological material, the method comprising:
provided a biological sample in a sampling position;
providing source light impinging on the biological sample such that, in response to such impinging light, light representative of the biological sample is produced along an emitted light path; and
positioning a light detector array in proximity to the biological sample and intersecting the emitted light path, and scanning the light detector array across a portion of the light representative of the biological sample.

28. The method of claim 27, wherein the source light is generated by a plurality of light emitting diodes or laser diodes.

29. The method of claim 28, further comprising providing source light at a first wavelength range and then providing source light at a second wavelength range that is substantially different from the first wavelength range.

30. The method of claim 27, wherein providing source light comprises providing excitation light that impinges on at least a portion of the biological material such that, in response to the excitation light, fluorescence representative of the biological sample is provided via the emitted light path for detection by the light detector.

31. The method of claim 30, further comprising filtering the source light to reduce interference between the source light and the light representative of the biological sample.

32. The method of claim 27, wherein the light detector array comprises a linear light detector array.

33. The method of claim 27, wherein the light detector array is scanned by translating the biological sample.

34. The method of claim 27, further comprising preventing light having the same or substantially the same frequency as the source light from impinging on the light detector.

35. A method for detecting an image relating to a biological sample, the method comprising:
providing a polynucleic acid chip having a sample of one or more polynucleic acid sequences thereon in a holder at a sampling position;
generating source light with one or more diodes;
impinging the source light on the sample to cause the sample to generate emitted light from at least a portion of the sample along an emitted light path, wherein the emitted light is generated by at least one of chemi-luminescence, fluorescence, chemi-fluorescence, phosphorescence, adsorption and photon excitation;
providing a light detector array in the emitted light path; and
translating the light detector array through at least a portion of the emitted light and detecting a plurality of images representative of the sample.

36. The method of claim 35, further comprising providing source light at a first wavelength range and providing source light at a second wavelength range that is substantially different from the first wavelength range.

37. The method of claim 35, further comprising filtering the source light to reduce interference between the source light and the emitted light generated from the biological sample.

38. The method of claim 35, further comprising preventing light having the same or substantially the same frequency as the source light from impinging on the light detector.

39. The method of claim 35, wherein the light path of the emitted light generated by the biological sample does not include any portion of the polynucleic acid chip.

40. A system for detecting a pattern of polynucleic acid hybridization in a biological sample, the system comprising:
a polynucleic acid chip holder to hold a polynucleic acid chip containing a sample in a sampling position;
a light source comprising one or more light emitting diodes positioned such that source light generated by the light source impinges on the sample and causes the portions of the sample to emit light along an emitted light path by at least one of chemi-luminescence, fluorescence, chemi-fluorescence, and photon excitation; and
a linear light detector array positionable in the emitted light path;
a scanning apparatus that translates the linear light detector across the light path to acquire a plurality of images representative of the sample.

41. The system of claim 40, wherein the light source comprises a first set of one or more diodes that generates light at a first wavelength range, and a second set of one or more diodes that generates light at a second wavelength range that is substantially different from the first wavelength range.

42. The system of claim 40, further comprising a source light filter adapted to reduce interference between the source light and the emitted light generated from the biological sample.

43. The system of claim 40, further comprising a lens assembly in the emitted light path such that at least a portion of the emitted light from the biological sample is focused on the light detector.

44. The system of claim 40, further comprising a chip transport mechanism having a plurality of chip holders and adapted to position a chip in a sampling position.

45. The system of claim 44, wherein the chip transport mechanism is a rotary mechanism.

* * * * *